US010660806B1

(12) United States Patent
Nelson-Herron et al.

(10) Patent No.: US 10,660,806 B1
(45) Date of Patent: May 26, 2020

(54) WHEELCHAIR SAFETY SYSTEMS AND RELATED METHODS

(71) Applicants: Blanche Michelle Nelson-Herron, Downey, CA (US); Gary B. Justice, Long Beach, CA (US)

(72) Inventors: Blanche Michelle Nelson-Herron, Downey, CA (US); Gary B. Justice, Long Beach, CA (US)

(73) Assignee: Blanche Michelle Nelson-Herron, Downey, CA (US)

( * ) Notice: Subject to any disclaimer, the term of this patent is extended or adjusted under 35 U.S.C. 154(b) by 0 days.

(21) Appl. No.: 16/743,506

(22) Filed: Jan. 15, 2020

(51) Int. Cl.
| | |
|---|---|
| *G08B 13/14* | (2006.01) |
| *A61G 5/10* | (2006.01) |
| *G16H 40/67* | (2018.01) |
| *G08B 21/02* | (2006.01) |
| *A61B 5/11* | (2006.01) |
| *G16H 80/00* | (2018.01) |

(52) U.S. Cl.
CPC .............. *A61G 5/10* (2013.01); *A61B 5/1112* (2013.01); *G08B 21/02* (2013.01); *G16H 40/67* (2018.01); *G16H 80/00* (2018.01); *A61G 2203/44* (2013.01)

(58) Field of Classification Search
None
See application file for complete search history.

(56) References Cited

U.S. PATENT DOCUMENTS

| | | | |
|---|---|---|---|
| 2,762,994 A | 9/1956 | Kennelly | |
| 4,320,385 A | 3/1982 | Bleiweiss et al. | |
| 4,840,391 A | * | 6/1989 | Schneider ................ A61G 5/10 248/121 |
| 6,702,314 B1 | 3/2004 | Crose | |
| 6,753,765 B2 | 6/2004 | Masuda | |

(Continued)

OTHER PUBLICATIONS

Jacob Kastrenakes, Intel announces 5G modem for phone, auto, and drone testing, The Verge, published online by theverge.com at least as early as Jan. 4, 2017, available online at https://www.theverge.com/2017/1/4/14165888/intel-5g-modem-announced, last visited Jun. 25, 2018.

(Continued)

*Primary Examiner* — Julie B Lieu
(74) *Attorney, Agent, or Firm* — Law Office of Paul B. Johnson; Paul Johnson

(57) ABSTRACT

A wheelchair system includes one or more servers. A software application is provided by the server(s) to be installed on a computing device (such as a mobile phone) communicatively coupled with the server(s) through a telecommunications network. One or more user interfaces displayed on the computing device, using the software application, include a traffic navigation selector configured to receive a user selection indicating that a wheelchair operator is preparing to cross a street. In response to a selection of the traffic navigation selector the software application may: determine whether vehicles are nearby; notify the wheelchair operator when to cross the street; notify the wheelchair operator how much time is left to cross the street; visually record the wheelchair operator crossing the street; and determine, based on receipt of sensory input from computing device sensors and wheelchair sensors, whether an accident has occurred and, if so, notify emergency personal and family/friends.

20 Claims, 24 Drawing Sheets

(56) References Cited

U.S. PATENT DOCUMENTS

| | | |
|---|---|---|
| 6,783,259 B1 | 8/2004 | Macedonio |
| 7,651,242 B1 | 1/2010 | Guerrant |
| 8,057,078 B1 | 11/2011 | Ko |
| 8,253,589 B2 | 8/2012 | Grimm et al. |
| 9,215,659 B2 | 12/2015 | Asrani et al. |
| 9,281,965 B2 | 3/2016 | Wakabayashi et al. |
| 9,421,909 B2 | 8/2016 | Strickland et al. |
| 9,505,412 B2 | 11/2016 | Bai et al. |
| 9,536,427 B2 | 1/2017 | Tonguz et al. |
| 9,675,507 B1 | 6/2017 | Wilson-Hunter |
| 9,692,510 B2 | 6/2017 | Ryan et al. |
| 9,881,503 B1 | 1/2018 | Goldman-Shenhar et al. |
| 10,182,952 B1 | 1/2019 | Nelson-Herron et al. |
| 2003/0156020 A1 | 8/2003 | Masuda |
| 2004/0092230 A1 | 5/2004 | Miyazaki et al. |
| 2005/0209769 A1 | 9/2005 | Yamashita et al. |
| 2006/0023446 A1 | 2/2006 | Racoosin |
| 2007/0132609 A1 | 6/2007 | Stackelhouse |
| 2007/0159354 A1 | 7/2007 | Rosenberg |
| 2009/0322558 A1 | 12/2009 | Videtich et al. |
| 2010/0141438 A1 | 6/2010 | Black |
| 2010/0214085 A1 | 8/2010 | Avery et al. |
| 2011/0018736 A1 | 1/2011 | Carr |
| 2011/0090093 A1 | 4/2011 | Grimm et al. |
| 2012/0046821 A1* | 2/2012 | Pettersson ................ A61G 5/04 701/25 |
| 2012/0268264 A1 | 10/2012 | Son |
| 2012/0306634 A1 | 12/2012 | Tsuda et al. |
| 2012/0314404 A1 | 12/2012 | Harshaw |
| 2013/0137372 A1 | 5/2013 | Nishidai |
| 2013/0218380 A1* | 8/2013 | Phillips .................. B60L 15/30 701/22 |
| 2014/0062685 A1 | 3/2014 | Tamatsu et al. |
| 2014/0142783 A1 | 5/2014 | Grimm et al. |
| 2014/0313761 A1 | 10/2014 | Nelson-Herron |
| 2015/0035685 A1 | 2/2015 | Strickland et al. |
| 2015/0091740 A1 | 4/2015 | Bai et al. |
| 2015/0116103 A1 | 4/2015 | Yang et al. |
| 2015/0149042 A1 | 5/2015 | Cooper et al. |
| 2015/0177362 A1 | 6/2015 | Gutierrez et al. |
| 2015/0197196 A1 | 7/2015 | Lin et al. |
| 2015/0228066 A1 | 8/2015 | Farb |
| 2015/0228195 A1 | 8/2015 | Beaurepaire et al. |
| 2015/0251599 A1 | 9/2015 | Koravadi |
| 2015/0332532 A1 | 11/2015 | Lee et al. |
| 2016/0205238 A1 | 7/2016 | Abramson et al. |
| 2016/0260328 A1 | 9/2016 | Mishra et al. |
| 2016/0277196 A1 | 9/2016 | Jose et al. |
| 2016/0277197 A1 | 9/2016 | Jose et al. |
| 2016/0335879 A1* | 11/2016 | Carr ..................... H04W 4/021 |
| 2016/0335895 A1 | 11/2016 | Lui et al. |
| 2016/0358471 A1* | 12/2016 | Hajj ................. G01C 21/3423 |
| 2017/0021760 A1 | 1/2017 | Calnek |
| 2017/0080952 A1 | 3/2017 | Gupta et al. |
| 2017/0279498 A1 | 9/2017 | Smith et al. |
| 2018/0050635 A1 | 2/2018 | Vincent et al. |
| 2018/0106906 A1 | 4/2018 | Mikami et al. |
| 2018/0120860 A1 | 5/2018 | Longin et al. |
| 2018/0208140 A1 | 7/2018 | Sugimoto et al. |
| 2019/0021921 A1* | 1/2019 | Nelson-Herron ........ B60Q 9/00 |

OTHER PUBLICATIONS

"First Responder Network Authority," Published online by Wikipedia at least as early as Nov. 14, 2019, available online at https://en.wikipedia.org/wiki/First_Responder_Network_Authority, last visited Nov. 14, 2019.

"OnStar," Published online by Wikipedia at least as early as Nov. 14, 2019, available online at https://en.wikipedia.org/wiki/OnStar, last visited Nov. 14, 2019.

\* cited by examiner

NAME: _____
MEDICAL: _____
MEDICARE: _____
ADA/DMV ACC CODE: _____
CELL: _____
WC MODEL: _____
_____
WEIGHT: _____

CONTACT1 NAME: _____
PHONE: _____ EMAIL: ____

CONTACT2 NAME: _____
PHONE: _____ EMAIL: ____

CONTACT3 NAME: _____
PHONE: _____ EMAIL: ____

[ ADD ]

ACKNOWLEDGMENTS: THE SAFETY SERVICES ARE ONLY AVAILABLE FOR WHEELCHAIR OPERATORS. ACCEPTANCE OF THE TERMS AND CONDITIONS AND CERTIFICATION WITH ADA/DMV CERTIFICATION CODE REQUIRED.

☐ I ACCEPT THE TERMS & CONDITIONS.

☐ I ACCEPT THE SOS NOTIFICATION TERMS.

[ CANCEL ] [ SUBMIT ]

FIG. 5  120

WHEELCHAIR SAFETY SYSTEMS AND RELATED METHODS

BACKGROUND

1. Technical Field

Aspects of this document relate generally to wheelchairs and other non-ambulatory devices.

2. Background Art

Wheelchair users at times find that vehicle operators do not notice them when the wheelchair users are crossing proximate vehicles (such as in front of, behind, or on the side of a vehicle). In some cases this is at least partly because the wheelchair-pedestrian is below (or near the bottom of) the view of the motorist's line of sight. This can cause accidents and injury to a wheelchair-pedestrian and/or damage to a vehicle. Whether a driver is driving forward, turning, backing up, etc., there is a danger to wheelchair-pedestrian in the area. While wheelchair flags and other visible mechanisms exist for safety (such as reflective members), there exists a need to keep wheelchair users safer from collisions with moving vehicles.

SUMMARY

Implementations of wheelchair systems may include: one or more servers; a software application provided by the one or more servers to be installed on a computing device communicatively coupled with the one or more servers through a telecommunications network; and one or more user interfaces displayed on the computing device using the software application, the one or more user interfaces displaying a traffic navigation selector configured to receive a selection indicating that a wheelchair operator is preparing to cross a street; the software application may be configured to: receive an input from one or more sensors of the computing device (hereinafter "computing device sensors"); determine, at least partly in response to receiving the input from the one or more computing device sensors, whether the wheelchair operator has been involved in an accident; and in response to determining that the wheelchair operator has been involved in the accident, automatically initiate sending of an accident notification to emergency personnel.

Implementations of wheelchair systems may include one or more or all of the following:

The one or more computing device sensors may include a global positioning system (GPS) sensor, an accelerometer, and a gyroscope.

The software application may be configured to determine, at least partly in response to receiving an input from one or more sensors coupled with a wheelchair (hereinafter "wheelchair sensors"), whether the wheelchair operator has been involved in the accident.

One of the one or more wheelchair sensors may be configured to sense a weight.

One of the one or more wheelchair sensors may be configured to sense motion of the wheelchair.

The software application may be configured to determine that the accident has occurred by determining that: the one or more wheelchair sensors have indicated that the wheelchair is not in motion; and/or the one or more wheelchair sensors have indicated that a weight has dropped below a predetermined threshold, and/or; the one or more computing device sensors have indicated a change in sensed values beyond a predetermined threshold.

The software application may be configured to, in response to the selection of the traffic navigation selector, provide a notification of an amount of time left to cross the street.

The software application may be configured to, in response to the selection of the traffic navigation selector, initiate visual recording of the wheelchair operator crossing the street using a camera communicatively coupled with the computing device through the telecommunications network.

One or more data stores may be communicatively coupled with the one or more servers, the one or more user interfaces may include an interface for initiating storing, in the one or more data stores, contact information of a contact person, and the software application may be configured to, in response to determining that the wheelchair operator has been involved in the accident, automatically send an accident notification to the contact person.

The software application may be configured to, in response to the selection of the traffic navigation selector, automatically initiate sending of one or more first signals, the software application may be configured to determine that one or more vehicles are within a predetermined area by receiving one or more return signals responsive to the one or more first signals, the software application may be configured to determine no vehicles are within the predetermined area by receiving no signals responsive to the one or more first signals within a predetermined amount of time, and the software application may be configured to notify the wheelchair operator, only after the software application has determined whether one or more vehicles are within the predetermined area, to proceed crossing the street.

The software application may be configured to initiate, in response to the selection of the of the traffic navigation selector, receiving the input from the one or more computing device sensors.

The software application may be configured to stop receiving the input from the one or more computing device sensors when the wheelchair operator reaches a predetermined distance from a communication node.

Implementations of wheelchair systems may include: one or more servers; a software application provided by the one or more servers to be installed on a computing device communicatively coupled with the one or more servers through a telecommunications network; and one or more user interfaces displayed on the computing device using the software application, the one or more user interfaces displaying a traffic navigation selector configured to receive a selection indicating that a wheelchair operator is preparing to cross a street; the software application may be configured to, in response to the selection of the traffic navigation selector, automatically initiate sending of one or more first signals; the software application may be configured to determine that one or more vehicles are within a predetermined area by receiving one or more return signals responsive to the one or more first signals; the software application may be configured to determine that no vehicles are within the predetermined area by receiving no signals responsive to the one or more first signals within a predetermined amount of time; and the software application may be configured to notify the wheelchair operator, only after the software application has determined whether one or more vehicles are within the predetermined area, to proceed crossing the street.

Implementations of methods of use of a wheelchair system may include: providing one or more servers; providing a software application, using the one or more servers, to be installed on a computing device communicatively coupled with the one or more servers through a telecommunications network; displaying one or more user interfaces on the computing device using the software application, wherein one of the one or more user interfaces includes a traffic navigation selector; receiving a selection of the traffic navigation selector using the one or more user interfaces, the selection of the traffic navigation selector indicating that a wheelchair operator is preparing to cross a street; receiving an input, using the software application, from one or more sensors of the computing device (hereinafter "computing device sensors"); receiving an input, using the software application, from one or more sensors coupled with a wheelchair (hereinafter "wheelchair sensors"); determining, using the software application, at least partly in response to receiving the input from the one or more computing device sensors and the input from the one or more wheelchair sensors, whether the wheelchair operator has been involved in an accident; and in response to determining that the wheelchair operator has been involved in the accident, automatically initiating sending of an accident notification to emergency personnel.

Implementations of methods of use of wheelchair systems may include one or all or any of the following:

The input from the one or more computing device sensors and the one or more wheelchair sensors may include one or more of: global positioning system (GPS) sensor data; accelerometer sensor data; gyroscope sensor data; weight data; and wheelchair motion data.

The method may include determining, using the software application, that the accident has occurred by determining that: the one or more wheelchair sensors have indicated that the wheelchair is not in motion; the one or more wheelchair sensors have indicated that a weight has dropped below a predetermined threshold, and; the one or more computing device sensors have indicated a change in sensed values beyond a predetermined threshold.

The method may include providing, using the software application, in response to the selection of the traffic navigation selector, a notification of an amount of time left to cross the street.

The method may include, using the software application, in response to the selection of the traffic navigation selector, initiating visual recording of the wheelchair operator crossing the street using a camera communicatively coupled with the computing device through the telecommunications network.

The method may include communicatively coupling one or more data stores with the one or more servers, the one or more user interfaces may include an interface for initiating storing in the one or more data stores contact information of a contact person, and the method may include automatically sending an accident notification to the contact person, using the software application, in response to determining that the wheelchair operator has been involved in the accident.

The method may include determining, using the software application, whether one or more vehicles are within a predetermined area based on whether one or more return signals have been received in response to one or more first signals, and the method may include notifying the wheelchair operator, using the software application, only after determining whether one or more vehicles are within the predetermined area, to proceed crossing the street.

General details of the above-described implementations, and other implementations, are given below in the DESCRIPTION, the DRAWINGS, and the CLAIMS.

BRIEF DESCRIPTION OF THE DRAWINGS

Implementations will be discussed hereafter using reference to the included drawings, briefly described below, wherein like designations refer to like elements:

FIG. 5 is an example of a user interface implemented using the system of FIG. 1;

DESCRIPTION

Implementations/embodiments disclosed herein (including those not expressly discussed in detail) are not limited to the particular components, mobile components, continuous integration/continuous development elements/tools, or procedures described herein. Additional or alternative components, assembly procedures, mobile components, developmental processes, and/or methods of use consistent with the intended wheelchair safety systems and related methods, including software applications, may be utilized in any implementation. This may include any materials, components, sub-components, methods, sub-methods, steps, application programming interfaces (APIs), Android Package Kits (APKs), software development kits (SDKs), frameworks, widgets, process steps, and so forth.

Wheelchair operators (WCOs) at times find that vehicles tend to not see them navigating traffic. When wheelchair operators are not seen in traffic they are less safe and, as a result, suffer a greater risk of an injury and even fatality. A vehicle travelling even at a lower speed, such as 15 miles per hour, can greatly injure or kill a wheelchair operator. However, motorists are often driving at faster speeds and are distracted. Wheelchair operators move much slower and are often operated by elderly persons or persons who cannot move rapidly. Wheelchair operators may need to be move close by a vehicle to navigate an intersection or cross a street. For example they can be in front of, behind, or on the side of a vehicle. The wheelchair operator may not be seen because they may be situated below (or near the bottom of) the motorist's line of sight.

Accidents between vehicles and wheelchair operators result in increased insurance claims/costs. Whether a motorist is driving forward, turning, backing up, and so forth, there is a risk to the safety of nearby wheelchair operators.

Some attempts have been made to reduce the risks to wheelchair operators. For example, flags or pennants of various colors have been attached to wheelchairs, bicycle poles have been used, and wheelchair operators have worn reflective vests, coats and jackets. Notwithstanding these efforts, the number of wheelchair/vehicle accidents has increased. Furthermore, as the number of autonomous vehicles rises, the effectiveness of reflective pennants and jackets and the like may be reduced.

Figure 1:
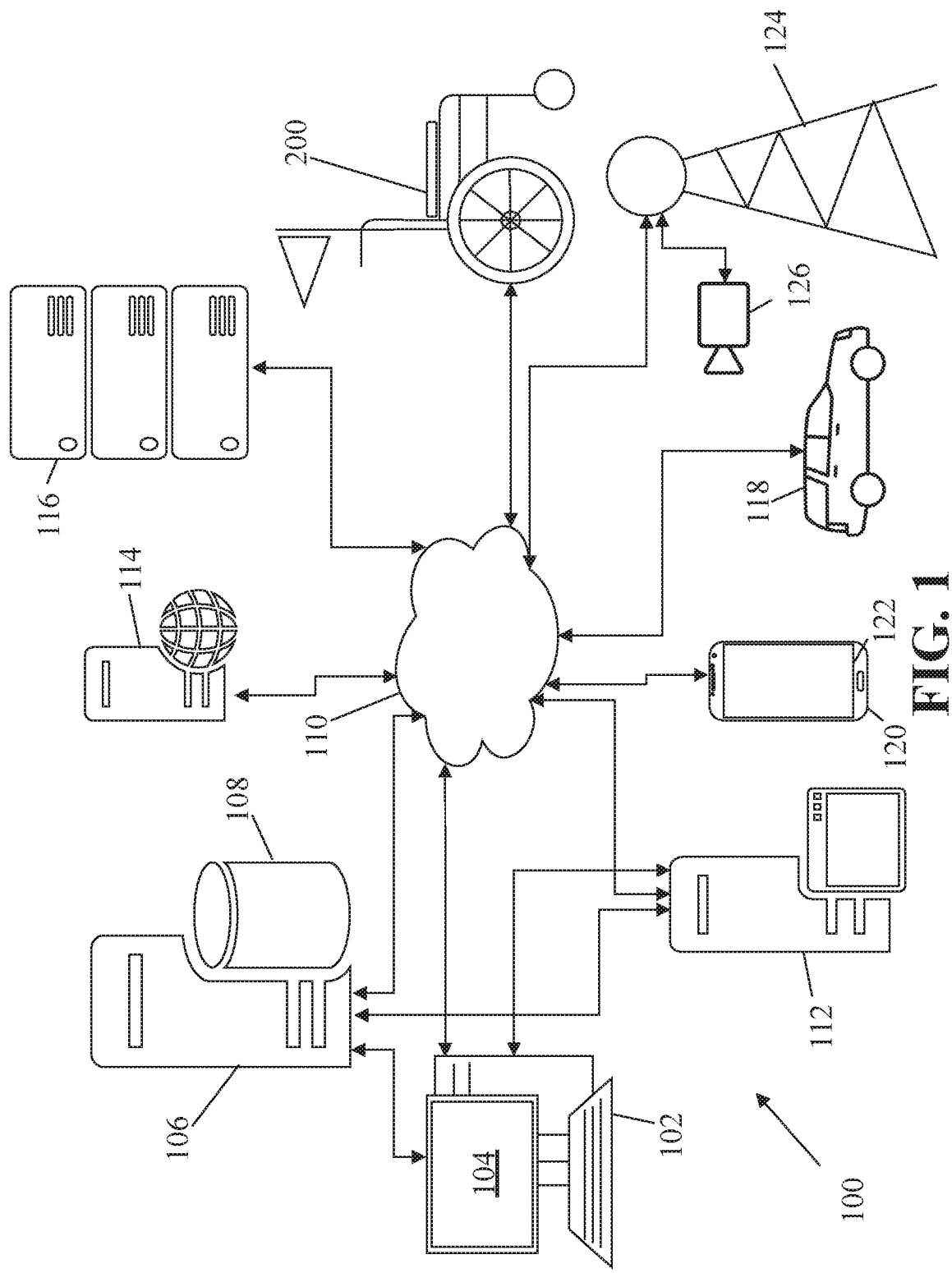
FIG. 1 is a diagram of an implementation of a wheelchair safety system (system)

Wheelchair safety systems and methods disclosed herein allow a wheelchair pedestrian to navigate safely near vehicles in transit. Referring to FIG. 1, an implementation of a wheelchair safety system (system) 100 is diagrammed. System 100 includes a computing device 102 having a display 104 upon which one or more user interfaces may be displayed to allow a user (such as an admin) to set up various elements of the system, such as by non-limiting example storing one or more elements in a database 108 by communication with a database server 106 either by direct connection (wired) or through a telecommunications network 110 such as, by non-limiting example, the Internet. The telecommunications network may include a variety of elements, including communication nodes such as cell towers, multiple-input and multiple-output (MIMO) towers, transceivers, wired and wireless components, and so forth. One MIMO tower 124 is shown, for instance, with a video camera 126 communicatively coupled thereto.

An application server 112 is shown, and this may be used to interface between a user (such as a wheelchair user or a driver) and the system (such as the database) through an application of a computer, smart device, smart phone, tablet, smart speaker, smart glasses, or any other computing device. A web server 114 is shown, which in implementations may be included to allow an admin, or wheelchair user, or driver to interface with the system via a website. One or more third party servers 116 may be used (for example the database server and database, application server, web server, and/or any other computing servers or the like) may actually be implemented using third party servers through a cloud connection. A wheelchair 200 is shown coupled with the system, as is a vehicle 118, which elements will be described in more detail hereafter.

Wheelchair systems in implementations may include additional elements or may exclude some of the elements shown in FIG. 1.

Figure 2:
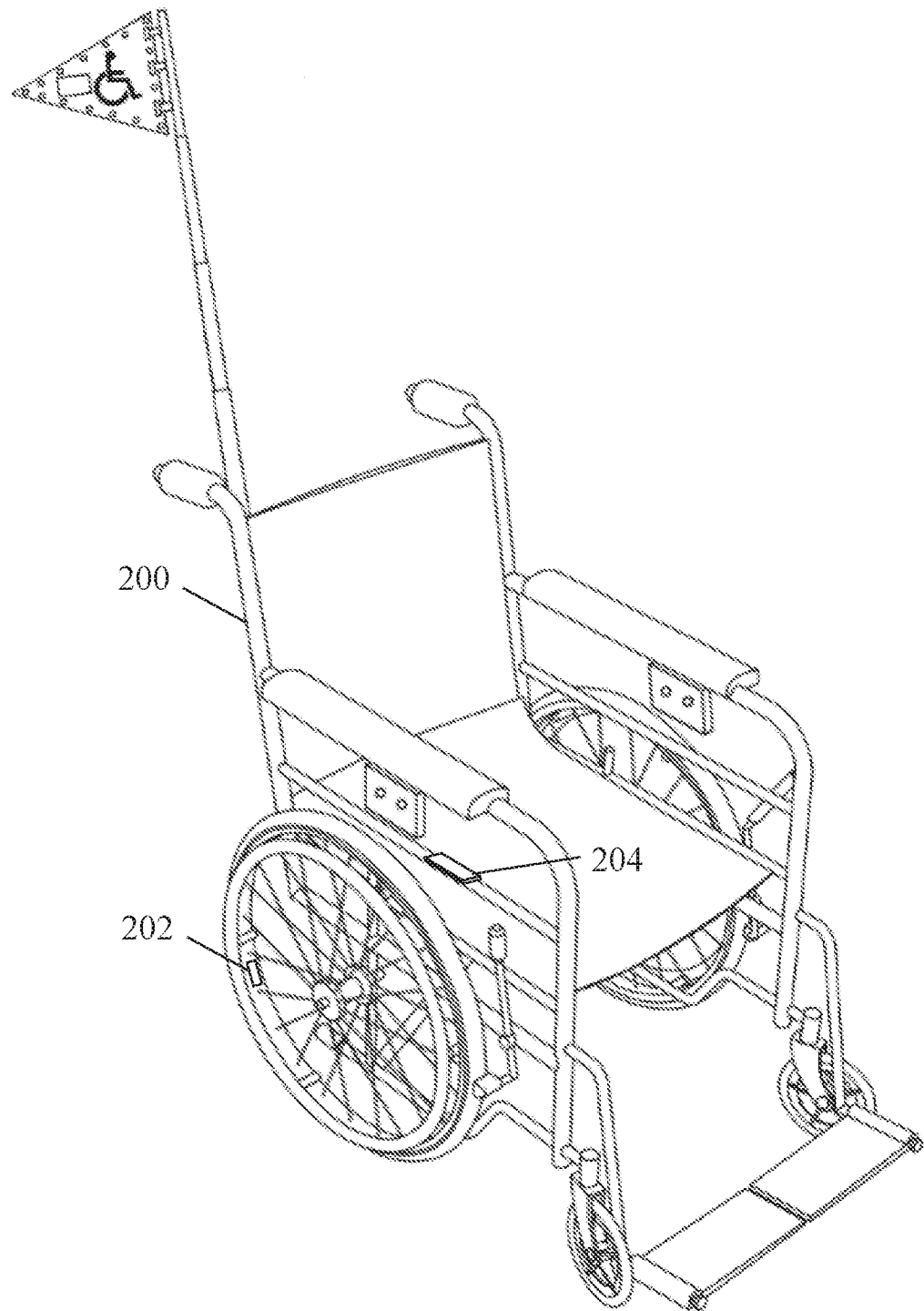
FIG. 2 is a front perspective view of an implementation of a wheelchair of the system of FIG. 1.

Referring now to FIG. 2, an implementation of a wheelchair 200 to be used in system 100 is shown. The wheelchair 200 and the system 100 and may include any elements described in U.S. Provisional Patent Application No. 62/536,080 entitled "Safe Sight," listing as first inventor Blanche Michelle Nelson-Herron, U.S. Patent Publication No. 2014/0313761 entitled "Wheel Chair Lighting," listing as first inventor Blanche M. Nelson-Herron, published Oct. 23, 2014, and U.S. Pat. No. 10,182,952 entitled "Wheelchair Systems and Related Methods," listing as first inventor Blanche Michelle Nelson-Herron, issued Jan. 22, 2019, the entire disclosures of each of which are incorporated herein by reference.

The aforementioned '952 patent discusses systems allowing a wheelchair pedestrian to communicate his/her presence to vehicles in traffic using an On Board Unit (OBU), such as a handheld device. Systems and methods disclosed herein do not require the use of an OBU as described in the '952 patent but utilize a software application running on a mobile device (such as computing device 120 of FIG. 1.

Implementations of system and methods disclosed herein may utilize FIRSTNET.GOV elements and services. Implementations of systems and methods disclosed herein may also utilize a 5G cellular infrastructure, such as using a 6 GHz band. In implementations a 4G environment restricts the application of very rapid notification of emergency services through a mobile app of the system. The software application running on the mobile device may interact with FIRSTNET.GOV elements and services, such as using cloud services associated with individual wheelchair operators.

Figure 8:
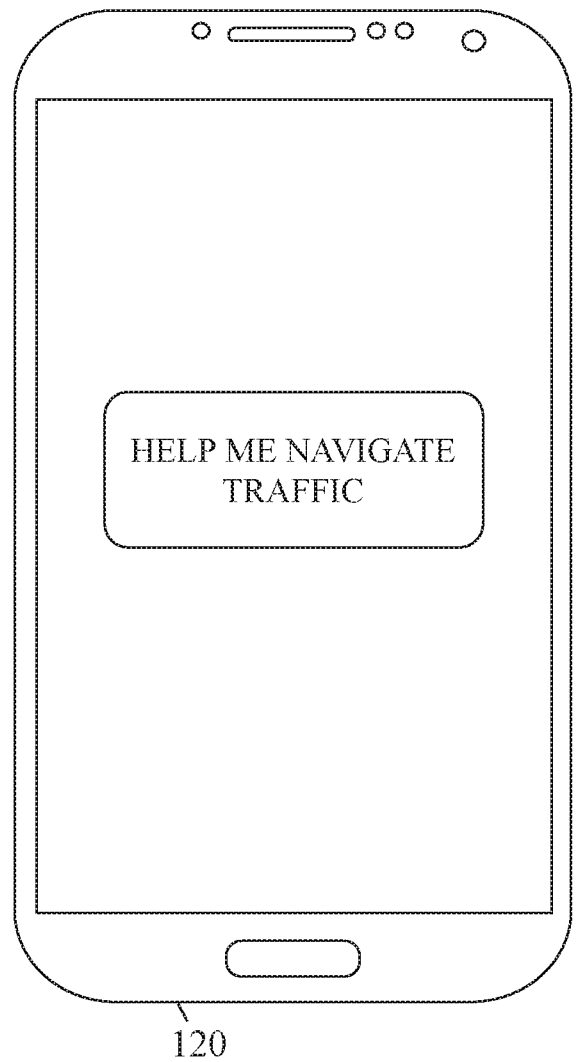
FIG. 8 is an example of a user interface implemented using the system of FIG. 1.

Referring briefly to FIG. 8, rather than tax the abilities of wheelchair operators by requiring them to interact with multiple screens of a mobile device, wheelchair operators in implementations may only need to select one selector to trigger safety features of the systems and methods. For example, when the wheelchair operator selects the "HELP ME NAVIGATE TRAFFIC" selector, the safety features may be implemented even if no other selectors have been selected on the same or other user interfaces of the computing device.

In implementations, in the case of an accident between a wheelchair operator and a vehicle, a three-event condition accident algorithm is triggered to issue emergency notifications. This may include communications with remote/cloud data servers such as FIRSTNET and Department of Motor Vehicles (DMV) servers and may further include sending notifications to the wheelchair operator's family members and/or local emergency medical services (EMS) personnel.

The systems and methods disclosed herein address the needs of wheelchair operators to be seen in traffic. When wheelchair operators are seen in traffic the risk of accidents with subsequent injuries and fatalities are reduced. In implementations the software application running on the mobile device uses the low latency capability associated with a 5G cellphone operating in a robust 5G cellular environment. Th 5G environment allows the wheelchair operator to, with a mobile device such as a cell phone, communicate with manually driven and autonomously driven/operated vehicles equipped with a Dedicated Short-Range Communication (DSRC) (or similar mobile sensing) device. The subsequent successful communication with manually driven and autonomous driven/operated vehicles will reduce the risk accidents of wheelchair operators and, at the same time, give wheelchair operators confidence in navigating the streets and intersections safely among manually driven and autonomously driven/operated vehicles.

In future years the number of autonomous vehicles may increase, and this may increase the risk of wheelchair/vehicle accidents. The systems and methods disclosed herein may help to reduce this risk.

In implementations the methods disclosed herein include equipping wheelchair operators with a 5G cellphone running a software application which can communicate in real time within the 5G infrastructure with manually driven and autonomous vehicles to inform and notify traffic that a wheelchair operator is in the local area. Even if the wheelchair operator is not visually seen, both the manually driven or autonomous vehicle and the wheelchair operator within range of a local MIMO tower are notified of the presence of each other in traffic.

The previously-described '952 patent utilizes a stand-alone on board unit (OBU). The methods and systems disclosed herein reduce the cost to the wheelchair operator by not requiring the separate OBU—rather, the wheelchair operator may utilize a software application running on a 5G cellular phone supported by a 5G infrastructure and achieve similar aims and/or functions of the claimed devices/methods/systems of the '952 patent. Accordingly, the software application running on the mobile device may mimic some of the safety features of the OBUs disclosed in the '952 patent. The systems and methods disclosed herein may also include additional features. For example, the systems and methods disclosed herein may include a time to cross countdown, and may also include the recording and uploading/downloading of intersection video clips.

The software application may have a login screen for a user to login and/or create an account. When an authorized wheelchair operator is signed in to the software application (referred to in places herein as the "iCu software application" or the "iCu app," the "iCu" portion being a shortened form of "I see you"), then through a sole selection of a "HELP ME NAVIGATE TRAFFIC" selector will initiate the implementation of communication between the wheelchair operator and manually driven or autonomous vehicles equipped with Dedicated Short-Range Communication (DSRC) (or similar mobile sensing) devices within the local MIMO area. When the crossing of the intersection is completed by the wheelchair operator and the wheelchair operator exits the range of the local MIMO tower, in implementations the iCu software application immediately turns off all safety functions.

In implementations the systems and methods disclosed herein may provide safety for the 3.5 million wheelchair operators navigating traffic. In implementations the systems and methods disclosed herein use server data and/or transform server data to enhance the safety of wheelchair operators in traffic. The persistent growth of traffic along with the burgeoning growth of the wheelchair community increases the need for wheelchair operator safety.

As indicated above, individual wheelchair operators have made efforts to be seen in traffic, such as by using flags, pennants and colored vests, with minimal effectiveness. Additionally, these visual aids may be even less effective for autonomous vehicles than manually-driven vehicles. The system features and methods disclosed herein represent an improvement to the technical field of wheelchair operator safety, and cannot feasibly be implemented without the computing systems/networks disclosed herein.

In implementations the accident algorithm includes a C++ derived software widget that governs the transfer of a digital safety signal to create an emergency notification as a result of an accident. In implementations the iCu software application accident algorithm may be used to activate one or more of the following safety-signaling features: LIFELINE medical alert devices, medical telemetry devices, airbags, etc. In implementations the iCu software application is used in conjunction with the wheelchair operator's 5G cellphone.

In implementations the iCu software application described herein is a simple two-dimensional, dynamic, mobile hybrid software application utilizing the FLUTTER Integrated Development Environment (IDE) platform supported by the DART programming language. The FLUTTER platform in implementations is useful due to its innate ability to provide the iCu software application using only one compiler for ANDROID, IOS, WINDOWS, and LINUX devices/systems. In implementations the system 100 may include 5G mobile devices (such as 5G mobile phones). In implementations the iCu software application functions better in a robust 5G cellular environment.

In implementations the iCu software application does not assume or negate existing DMV, traffic governance or pedestrian regulatory policies. In implementations one purpose of the iCu software application is to cull raw data from cloud servers and transform this data into safety information screens (user interfaces) usable by wheelchair operators in their attempt to navigate traffic-laden intersections.

In implementations four safety features of the iCu software application are: (1) the iCu software application through the MIMO tower provides an audible and/or visible recommendation to the wheelchair operator before crossing the intersection to "PROCEED WITH CAUTION;" (2) the iCu software application captures a short (by non-limiting example, 10-20 second) video clip of the intersection crossing and downloads the video clip from the MIMO tower to the mobile device (by non-limiting example, a 5G cellphone); (3) the iCu software application receives a download of the time-to-cross status (for example in seconds) to the wheelchair operator's mobile device before the wheelchair operator enters the intersection; (4) the iCu software application is equipped with a three-condition event accident algorithm that, when triggered by an accident incident, issues a notification from FIRSTNET and/or DMV cloud services to notify local EMS providers and to notify family/friends of the wheelchair operator. In implementations, instead of a video, the visual recording could for example include recording a series of photographs instead of recording a video. In some implementations audio recording may be performed as well, such as a combined audiovisual recording.

The operation and execution of the safety functions described above will be discussed by reference to the figures, including user interfaces (UIs)/screens referenced below that appears on the wheelchair operator's mobile device (by non-limiting example, a 5G cellphone), to guide them to safety while in traffic.

Figure 3:
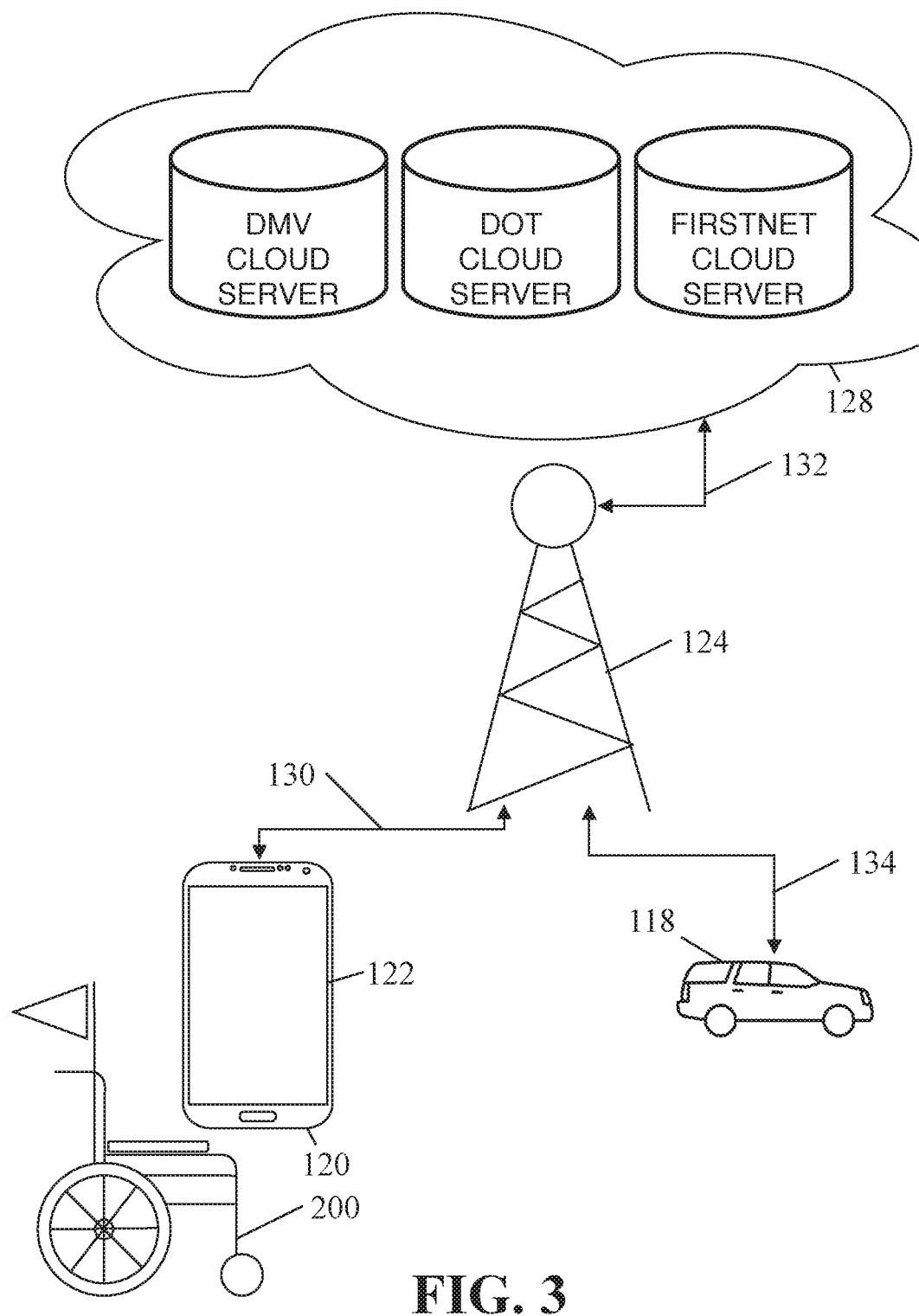
FIG. 3 is a diagram representatively illustrating elements and methods of the system of FIG. 1.

Referring now to FIG. 3, a use case diagram is shown which identifies communication paths and data routes between elements of system 100 during traffic. In this representative example the telecommunications network includes a 5G mobile cellular network which includes the following nodes: a 5G cellphone (computing device 120) operated by a wheelchair operator of wheelchair 200, a local area MIMO tower 124, cloud servers 128, and a DSRC (or similar sensing device) (not shown in FIG. 3, but located in/on vehicle 118 which may be a manually driven vehicle or an autonomous vehicle). Communication links/paths 130, 132, 134 between the elements are representatively illustrated in FIG. 3. Communication link 130 represents a wireless communication link (uplink/downlink) between device 120 and the MIMO tower 124. Communication link 132 represents a communication link (uplink/downlink) (that may include some wired and some wireless components) between the local MIMO tower and the cloud data servers 128. Communication link 134 represents a wireless communication link (uplink/downlink) between the local MIMO tower and the DSRC (or similar sensing device) of the vehicle 118.

Figure 4:
FIG. 4 is an example of a user interface implemented using the system of FIG. 1.

FIG. 4 representatively illustrates a branding screen which may be displayed to the wheelchair operator upon first signing into the software application or at any other time. The representative branding shown in FIG. 5 is TLM which represents "Together Lives Matter." The branding screen may be shown to a user before the user has applied to be an authorized user.

FIG. 5 shows an application profile authorization screen that is filled out by the wheelchair operator annually to gain access to the iCu Software application. As can be seen the form asks for the user's name, medical information, MEDICARE information, ADA/DMV access code, cell phone number, wheelchair model, weight (of the user and/or the wheelchair), contact information for family members and/or friends to be contacted during an accident, and additional explanation and selectors to accept terms and conditions (which may be reviewed by clicking on the TERMS AND CONDITIONS link) and to the sharing of accident information with family/friends that the user has designated (which terms may be viewed by clicking the SOS NOTIFICATION TERMS link). The system 100 may automatically require the wheelchair operator to update this information annually, such as by providing notifications to the wheelchair operator. The wheelchair operator could add three contacts, including names, phone numbers and email addresses, on the interface of FIG. 5 or could select the ADD selector to add additional contacts. Once the form is fully filled out the user may select SUBMIT to submit the data, which will then be uploaded to and processed by one or more servers of system 100 and/or stored in one or more databases of system 100 (including third party servers such as the DMV, FIRSTNET, and DOT cloud servers). The user may alternatively select the CANCEL selector to cancel.

Figure 6:
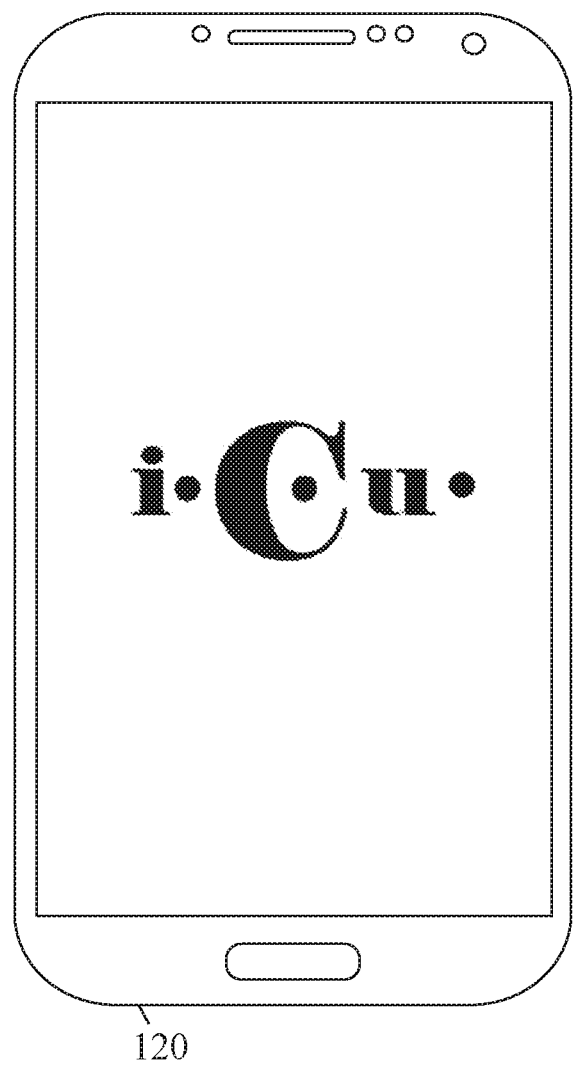
FIG. 6 is an example of a user interface implemented using the system of FIG. 1.

FIG. 6 shows a representative example of a download screen or an "application acceptance" or "authorization for use" screen which may be shown to the user to indicate that the application has been accepted or properly processed and that the software application is downloading to the mobile device or has not yet completed installing.

Figure 7:
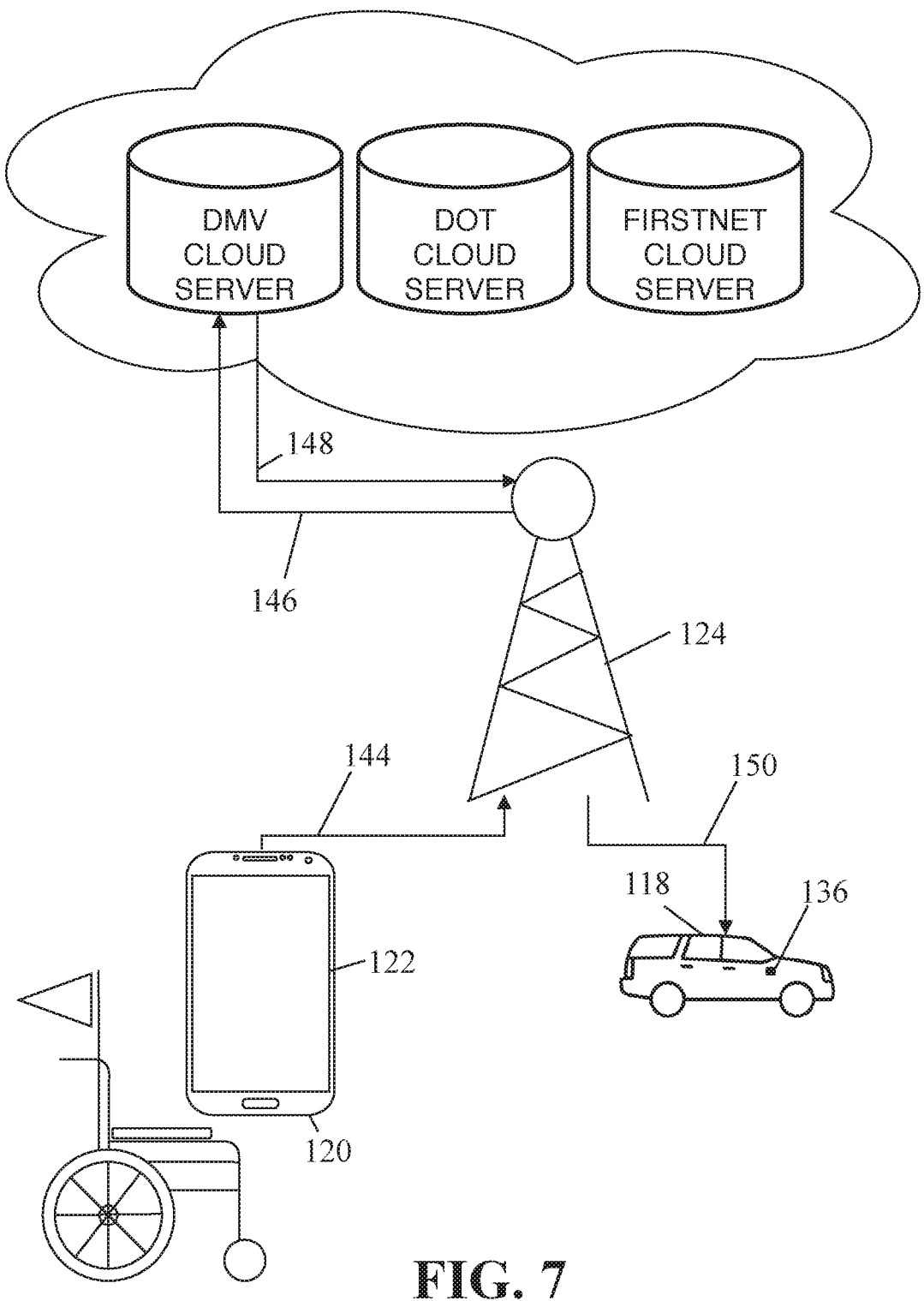
FIG. 7 is a diagram representatively illustrating elements and methods of the system of FIG. 1.
Figure 22:
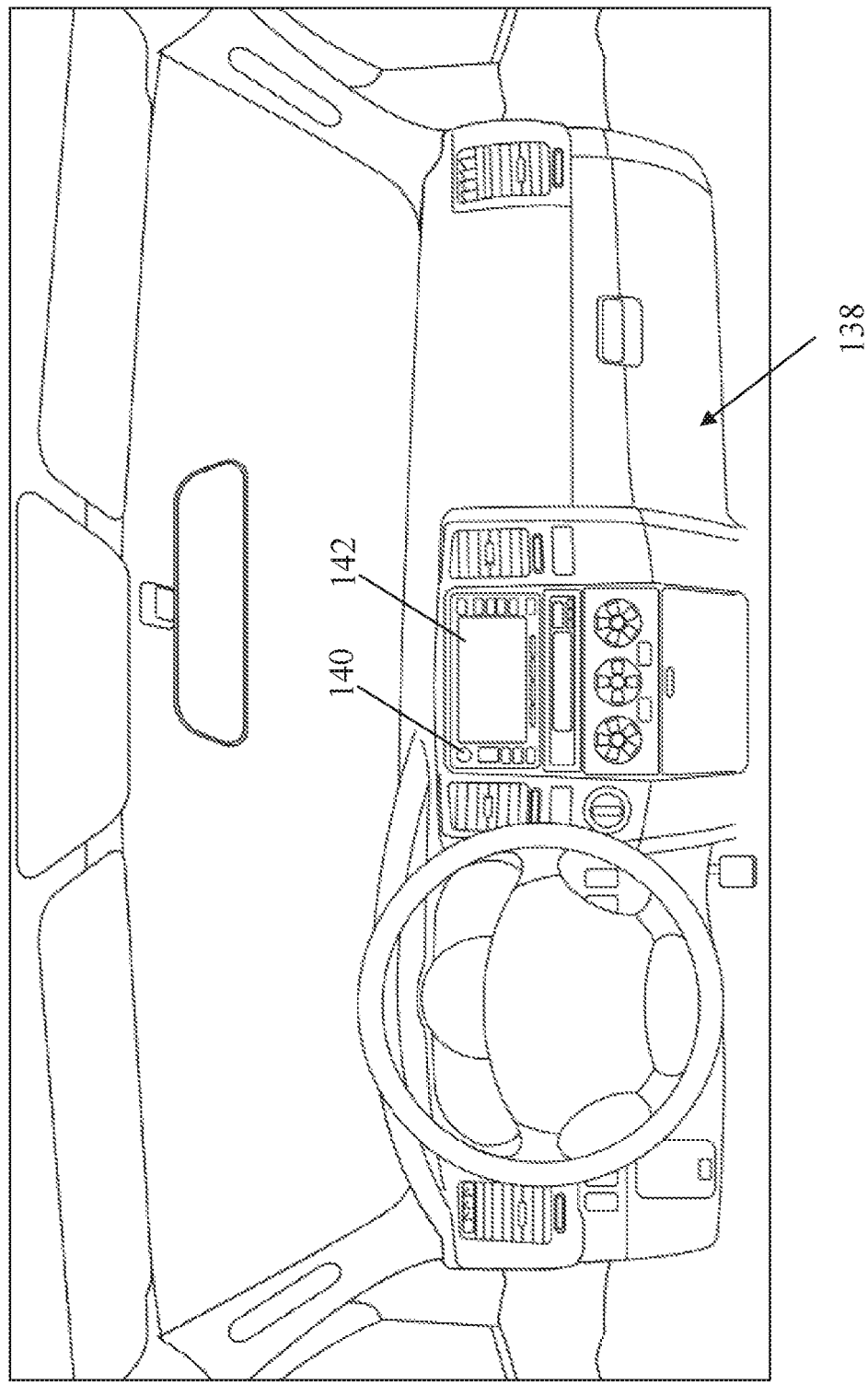
FIG. 22 is a dashboard view of a vehicle of the system of FIG. 1.

Referring now to FIG. 7, a use case diagram representatively illustrates the initializing of communications from the mobile device of a wheelchair operator to a vehicle, which in implementations may be a manually-driven vehicle or an autonomous vehicle. When the DSRC (or similar sensing device) 136 of the vehicle receives a Basic Safety Message (BSM) from the wheelchair operator a light (or similar indicator) may appear on the dashboard of the vehicle, alerting a passenger and/or driver of the vehicle that the wheelchair operator is in the local area. For example, FIG. 22 representatively illustrates a dashboard 138 of the vehicle, which includes a light 140 and a display 142. The alert or notification may be displayed on the display, and/or may be indicated by the light illuminating or flashing (or illuminating with a specific color), and/or may be presented to the passenger/driver as an audio notification delivered through the speakers of the vehicle.

The method of use representatively illustrated in FIG. 7 includes the wheelchair operator selecting the "HELP ME NAVIGATE TRAFFIC" selector (shown in FIG. 8) on a user interface of mobile device 120. In implementations, after a user has submitted the aforementioned application and successfully installed the software application on the mobile device, whenever thereafter the user opens the software app on the mobile device the "HELP ME NAVIGATE TRAFFIC" selector is clearly displayed on a screen/interface (it could be the first interface upon opening or an interface shown after a branding and/or loading interface). Accordingly, when the software app is running the user may, through the selection of a single selector, initiate the traffic navigation assistance. The use of the phrase "HELP ME NAVIGATE TRAFFIC" is just one representative example of what this selector could display—in other examples it could display other wording or even an image without wording.

In response to the wheelchair operator selecting the "HELP ME NAVIGATE TRAFFIC" selector (which may also be called a traffic navigation selector) the mobile device sends an uplink BSM signal 144 to the DMV cloud server/database through the local MIMO tower. Specifically, signal 144 represents the uplink of the BSM signal to the MIMO tower and signal 146 represents the MIMO tower routing the signal to the DMV cloud server through an uplink. The DMV cloud server processes the signal and generates a signal 148 which is sent to the MIMO tower to send it to the vehicle, and signal 150 represents the MIMO tower communicating the signal to the DSRC (or similar device) of the vehicle. The visual and/or audio notification is then given to the vehicle and/or its occupant(s), indicating that a wheelchair operator is nearby navigating traffic.

In implementations the "HELP ME NAVIGATE TRAFFIC" selector is selected by the wheelchair operator at every intersection to be crossed.

Referring to FIG. 8, which has been described previously, the "HELP ME NAVIGATE TRAFFIC" selector is shown. The user only needs to select this selector once when navigating traffic (for example once at each intersection).

Figure 9:
FIG. 9 is an example of a user interface implemented using the system of FIG. 1.

In implementations, while the aforementioned signals are being sent, and until a return signal is received by the device 120, a user interface of device 120 may display a screen similar to that shown in FIG. 9. FIG. 9 shows a screen which states that a request (the BSM signal) has been sent and that the software application is waiting for an acknowledgment signal to be received by the device 120. In implementations in which system 100 includes elements of a 5G environment the signal routing may occur so rapidly (low latency) that the interface of FIG. 9 is not displayed but, in such implementations, the interface of FIG. 9 could be shown when the user has filled out the authorization form of FIG. 5 and until the system sends a return signal to the device 120 that the form was properly submitted, to indicate to the wheelchair operator that the form has been submitted and that the software app is waiting for device 120 to receive an acknowledgment.

Figure 10:
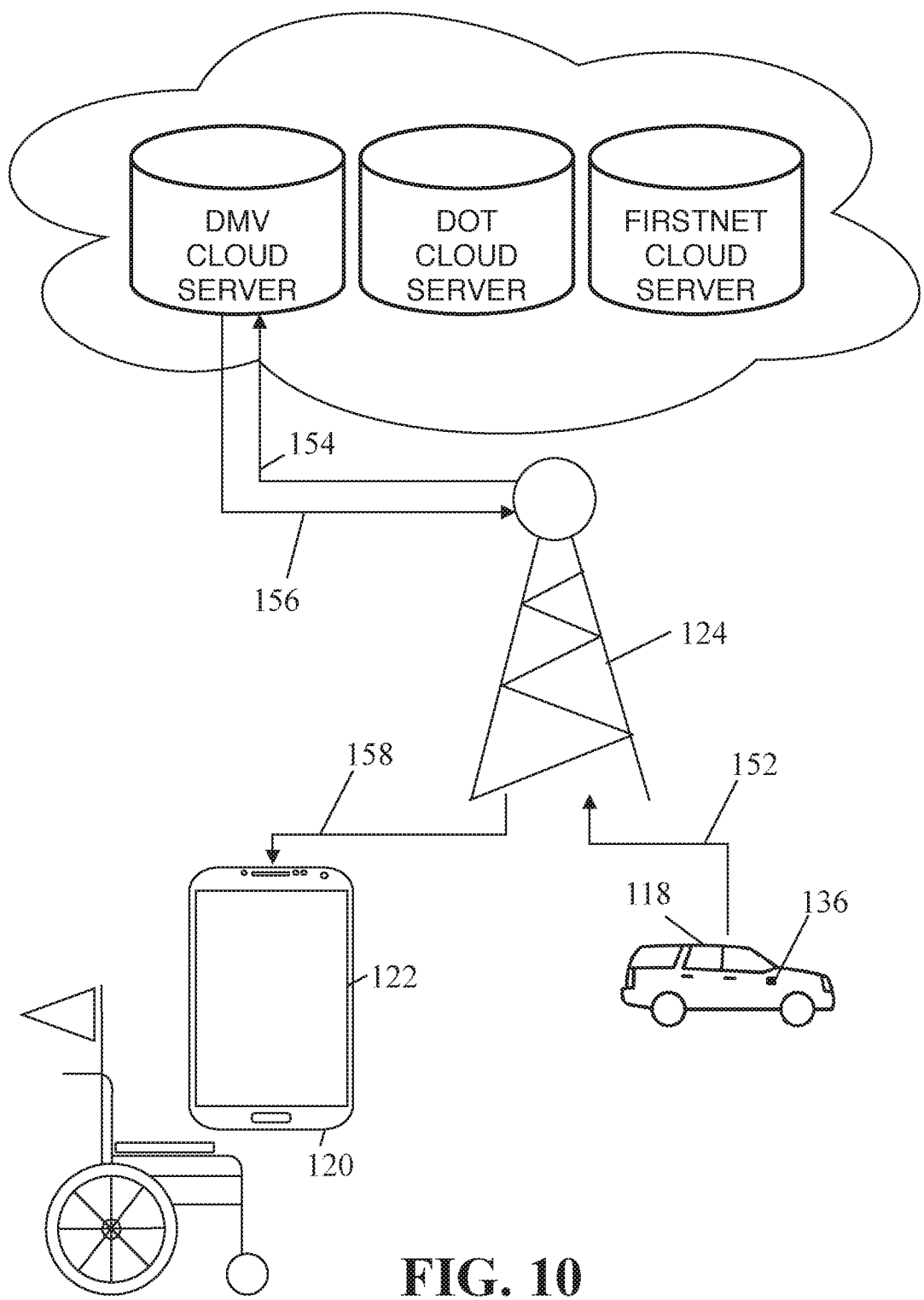
FIG. 10 is a diagram representatively illustrating elements and methods of the system of FIG. 1.

Referring now to FIG. 10, a use case diagram is shown which representatively illustrates a response communication from the vehicle to the mobile device of the wheelchair operator through a telecommunications network, such as using a 5G cellular environment and cloud databases. In the implementation shown, an acknowledgment signal is uplinked from the DSRC (or similar device) to the local area MIMO tower (signal 152), from the MIMO tower to the DMV cloud server (signal 154), is processed by the DMV cloud server and a signal sent to the MIMO tower (signal 156) and then sent from the MIMO tower to device 120 (signal 158). In implementations, in response to receiving this acknowledgment signal an audible and/or visual message or notification, such as using the mobile device's speakers and/or display, notifies the wheelchair operator.

Figure 11:
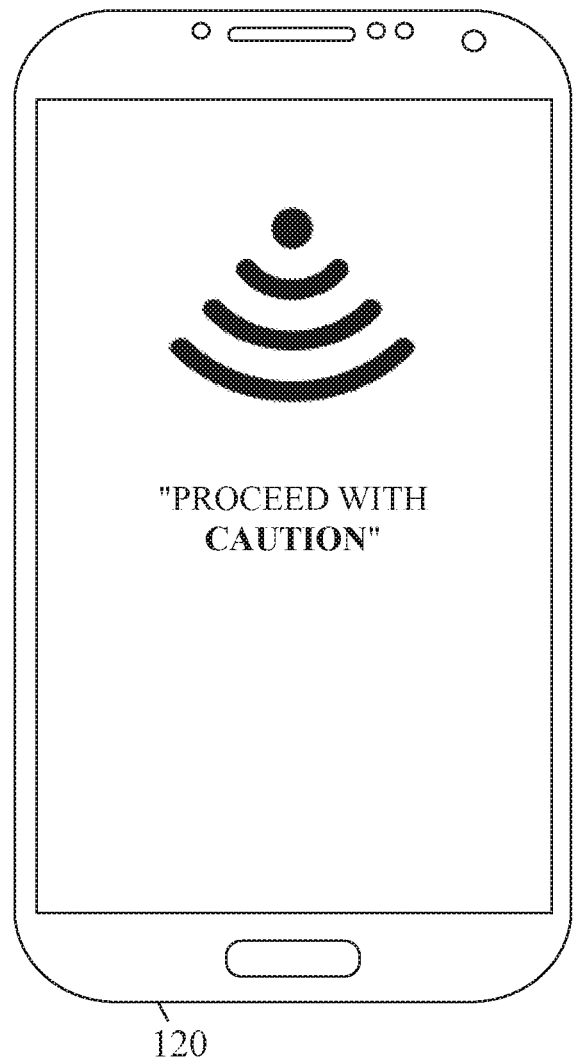
FIG. 11 is an example of a user interface implemented using the system of FIG. 1.

This could include a visual display as shown on the interface of FIG. 11 indicating to the wheelchair operator to "PROCEED WITH CAUTION." This notification could be spoken to the user using the mobile device's speakers. A sound notification (such as a distinctive sound) could also be used and/or a light lighting up or flashing (and/or using a specific color) may be displayed on the display or one of the lights of the mobile device. The "PROCEED WITH CAUTION" wording is only one example of wording that could be used, and another phrase (or an image with no words) could indicate to the wheelchair operator to proceed. In some implementations if no acknowledgment signal is received, the "PROCEED WITH CAUTION" notification could be presented after sufficient time has passed to receive acknowledgment signals, or another notification such as "NO VEHICLES DETECTED" or "NO INTERSECTION TRAFFIC" could be presented to the user. The amount of time sufficient to receive an acknowledgment signal depends on various factors but could be, by non-limiting example, 5, 10, 15, 20, 25, 30, 35, 40, 45, 50, 55, or 60 seconds. If no acknowledgment signals have been received by the predetermined amount of time, this may be used by the system to determine that no vehicles are in the MIMO area. In implementations a notification such as "NO INTERSECTION TRAFFIC" or the like is, effectively, a notification to begin crossing the street/intersection. Any given acknowledgment signal may indicate that the vehicle sending it is within the range of the MIMO tower (a predetermined area), though in other implementations methods may be used to determined a range broader than the MIMO tower (such as using GPS signals and multiple MIMO towers) or a range smaller than the entire MIMO tower range (such as using GPS signals).

Figure 12:
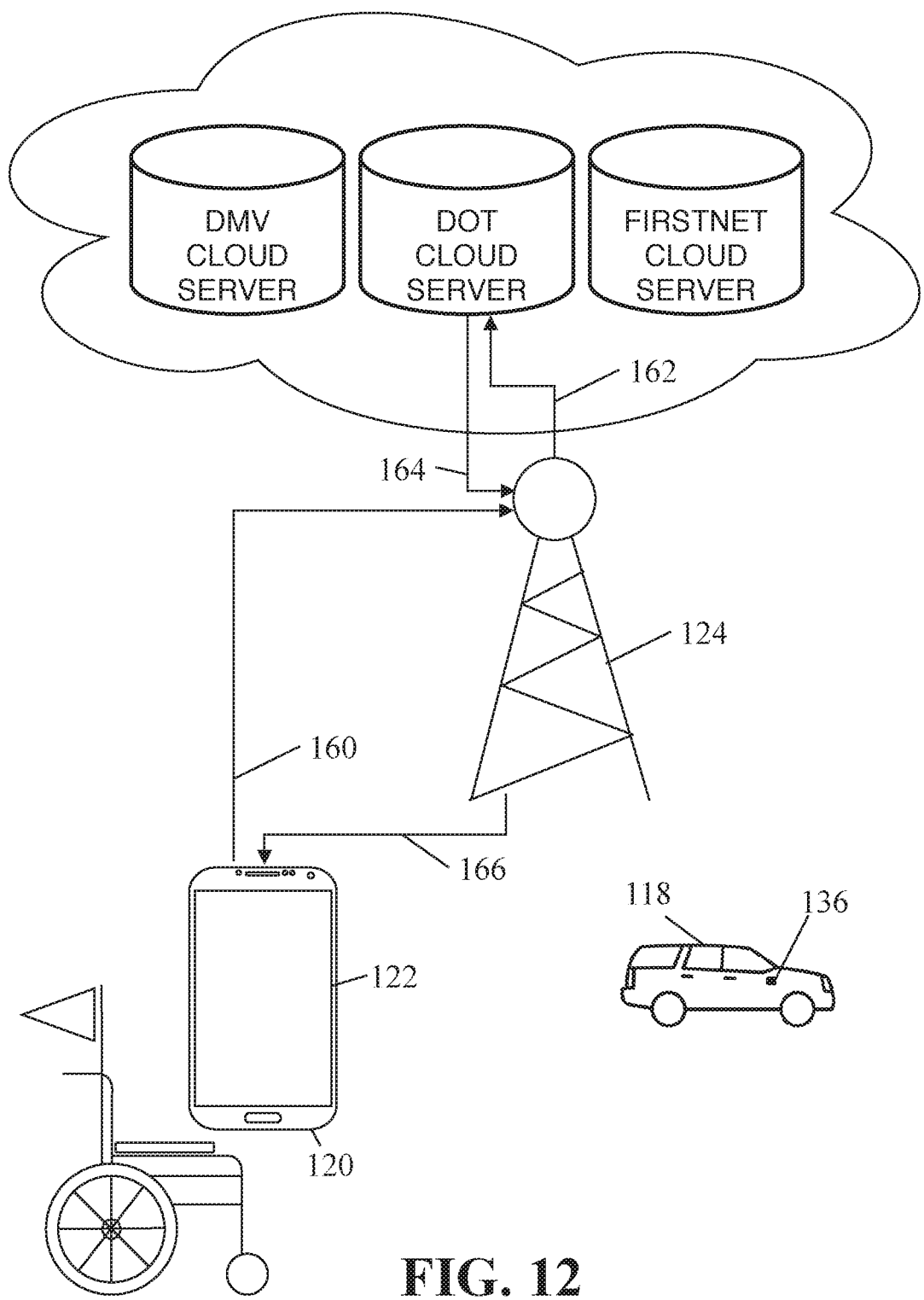
FIG. 12 is a diagram representatively illustrating elements and methods of the system of FIG. 1.

Referring now to FIG. 12, a use case diagram representatively illustrates safety features provided to the wheelchair operator through the use of a Department of Transportation (DOT) cloud database/server. In this implementation the mobile device may send one or more signals (signals 160/162) to the DOT cloud server through the MIMO tower, such as the GPS position of the mobile device, so that DOT cloud server may determine which intersection and which street, in which direction, the wheelchair operator is crossing. The DOT cloud server then downloads do the mobile device, in real time, signals 164/166 which communicate to the mobile device the time remaining for the wheelchair operator to cross the intersection. The initial time to cross is made available to the wheelchair operator prior to his/her beginning to cross the intersection. The DOT database/server (and/or databases/servers of related agencies) may provide this data by deriving it from local area video surveillance cameras and/or intersection timing codes/settings on local area traffic lights (for example the timing settings of a traffic light of a specific intersection being crossed).

Figure 13:
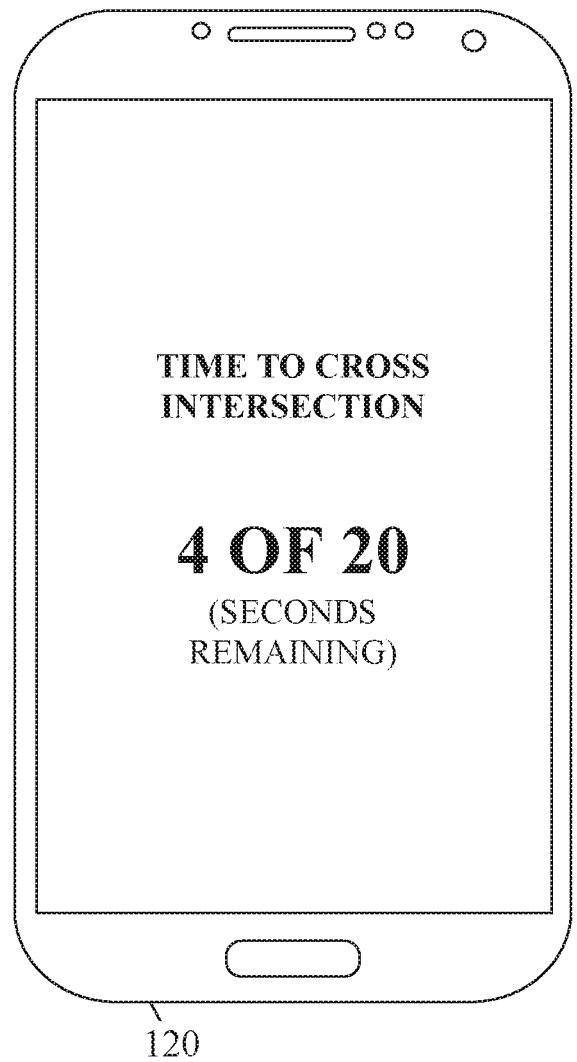
FIG. 13 is an example of a user interface implemented using the system of FIG. 1.

Referring now to FIG. 13, a time to cross countdown is shown on an interface of the wheelchair operator's mobile device in response to receiving signal 166. The countdown could also be provided in audio format through the mobile device's speakers in response to receiving signal 166. The signals 160/162 and 164/166 may be occurring continuously during any given street crossing, so that the DOT cloud server is being updated with the real time GPS position of the wheelchair operator and the wheelchair operator is being updated with the time left to cross.

Figure 14:
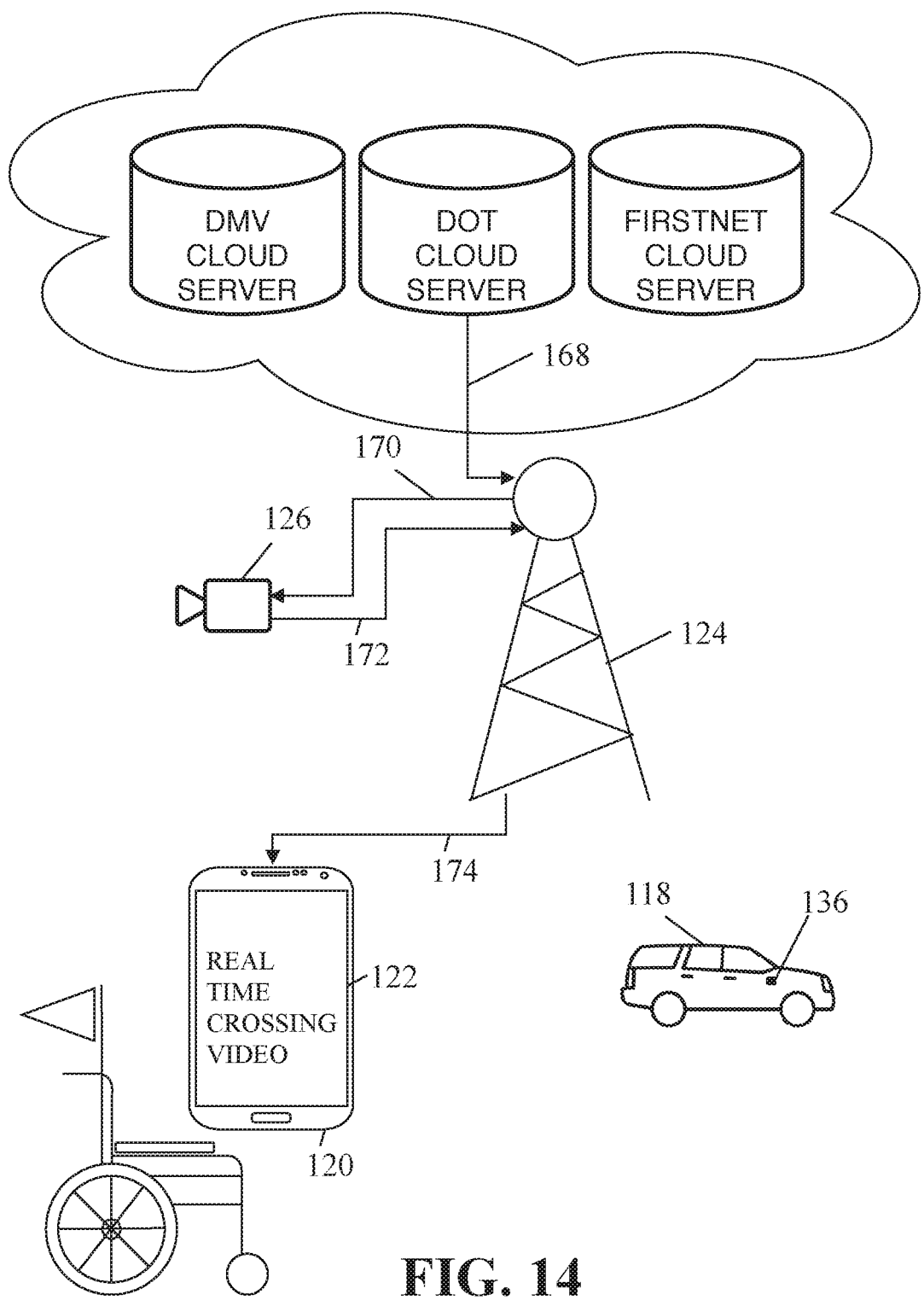
FIG. 14 is a diagram representatively illustrating elements and methods of the system of FIG. 1.

FIG. 14 representatively illustrates a use case diagram of a safety feature provided by the DOT cloud database/server to a wheelchair operator attempting to cross an intersection. In this example the DOT cloud database/server has already received (or is continuously receiving) signals 162 regarding the GPS position of the mobile device. The MIMO tower in this implementation is communicatively coupled with a video camera 126. In some implementations the video camera could be attached directly to the MIMO tower though, in other implementations, it could be located at an intersection remote from the MIMO tower but within the range of the MIMO tower to wirelessly communicate with the MIMO tower.

The DOT cloud server sends a signal 168 to the MIMO tower, which then sends signal 170 to the video camera to initiate recording at the intersection. The video camera captures a video clip of the intersection to record the wheelchair operator crossing the intersection. The video camera then sends signal 172 to the MIMO tower including the recorded data, and the data is downloaded to the mobile device 120 through signal 174 from the MIMO tower. In implementations the DOT database/server (and/or databases/servers of related agencies) may initiate the video recording using local area video surveillance cameras. The video clip may be timed, for example in implementations it could be a 10-20 second clip, though the specific timing of the clip may be determined using intersection timing codes on local area traffic lights (such as the specific light at the location of the crossing). In implementations the video could be recorded until the GPS position of the mobile device indicates that the wheelchair operator has finished crossing the street. In implementations, in addition or alternative to downloading the video to the mobile device, the video may be uploaded to the DOT cloud server or another server so that the wheelchair operator and/or law enforcement and the like could stream the video when desired.

Figure 15:
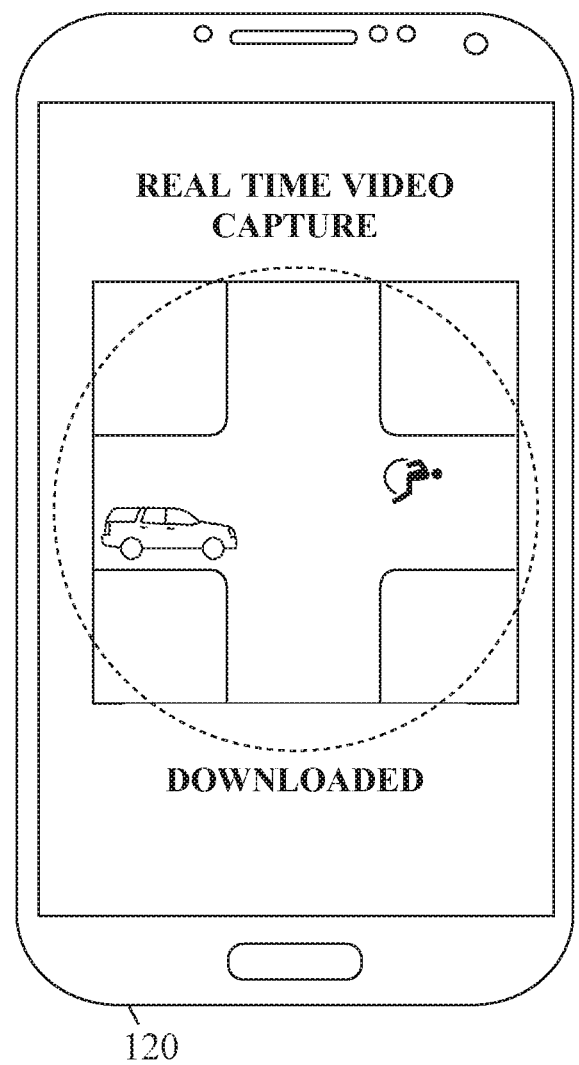
FIG. 15 is an example of a user interface implemented using the system of FIG. 1.

Referring now to FIG. 15, a user interface (UI) of the wheelchair operator's mobile device is representatively illustrated. This is an intersection crossing screen/UI and shows a real-time video clip of the intersection crossing. The dotted/dashed circle on this interface represents a display of the local area bounded by the MIMO tower. In this implementation the local area comprises a radius of 120 yards. In this local area is where the safety features may be invoked. After the wheelchair operator is beyond the 120 yards distance (or, for example, some other distance) from the MIMO tower, the software application of the mobile device may be reset, with the user needing to select the "HELP ME NAVIGATE TRAFFIC" button again to activate it. Until this selector is selected again, the software application may stop gathering information from the wheelchair sensors, the phone sensors, and so forth. Elsewhere herein the radius of the MIMO tower is termed a "predetermined distance" from the MIMO tower (communication node).

Figure 16:
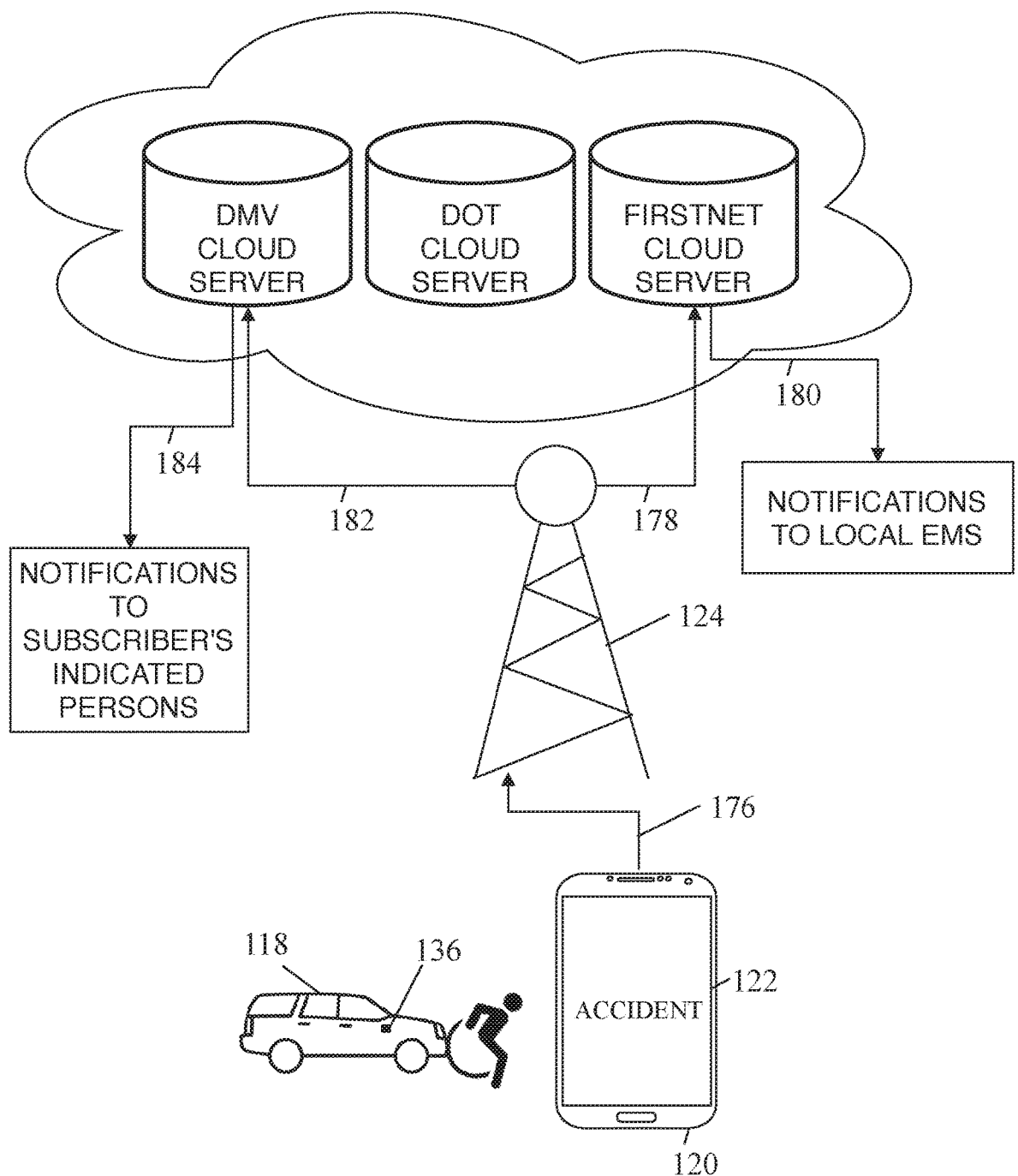
FIG. 16 is a diagram representatively illustrating elements and methods of the system of FIG. 1.

Referring now to FIG. 16, a use case diagram of an accident & emergency notification process is representatively illustrated. This process occurs when a wheelchair operator is involved in an accident. In implementations an accident is determined by a three-condition event accident algorithm. When an accident occurs as determined by the accident algorithm the software app of the mobile device 120 sends an emergency notification signal 176 to the MIMO tower which is routed to the DMV cloud server through signal 182 and to the FIRSTNET cloud server through signal 178 (in implementations the two signals that are routed in this way may be identical signals). The DMV.gov database/servers (cloud services) may be used to automatically notify family members, friends, or other stored contacts of the subscriber (wheelchair operator) through one or more signals 184, which may be routed through the Internet, for example. The FIRSTNET.gov database/servers may be used to automatically notify local emergency medical services (EMS) through one or more signals 180, which may be routed through the Internet, for example. The FIRSTNET database/servers may be used to notify local EMS personnel to help the specific wheelchair operator involved in an accident. In implementations this may be facilitated at least partly by the system 100 and its elements accessing data of the FIRSTNET database/servers using, for example, MYSQL functions of the system 100 (for example the iCu software application or other elements). In implementations this functionality could also involve the FIRSTNET servers accessing one or more databases of system 100.

Figure 17:
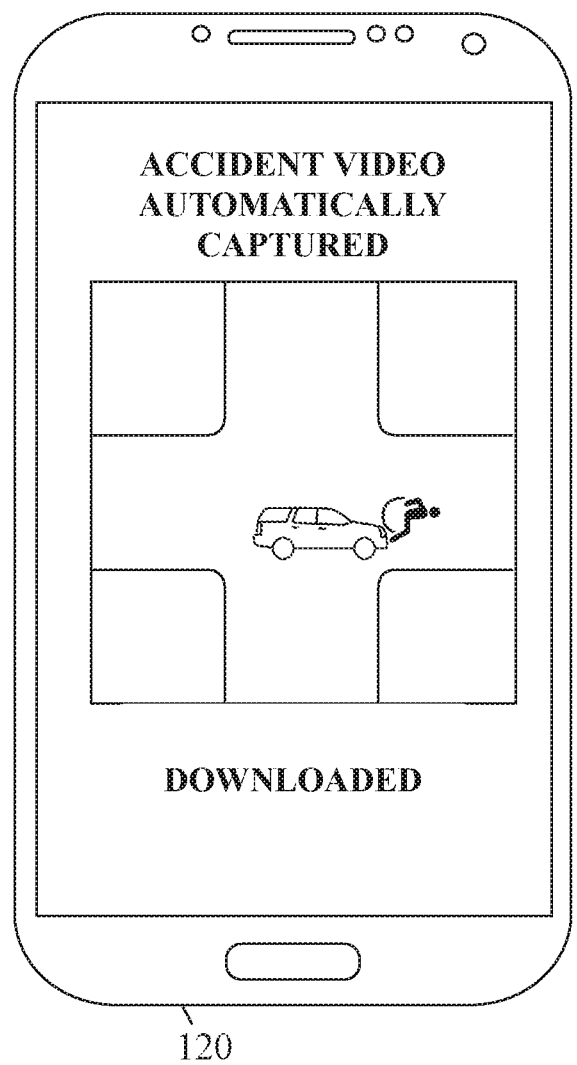
FIG. 17 is an example of a user interface implemented using the system of FIG. 1.

FIG. 17 representatively illustrates the accident as captured by the video camera and downloaded to or streamed from the mobile device 120. FIG. 17 representatively illustrates an overhead view. In implementations the recorded view may be a side, front, rear, or other angled/perspective view of the accident. In implementations multiple views may be captured by different video cameras and each view may be accessible by being downloaded to the mobile device or stored in the DOT cloud server/database and streamed as desired. For example, a first video of an overhead view of the accident and a second video showing a front or side view of the accident may be recorded and available for viewing.

In implementations the DMV database/server may store data associated with the wheelchair operator that the wheelchair operator supplies through the one or more user interfaces of the mobile device (such as an application interface for becoming an authorized user) as shown in the drawings. For example this may include wheelchair type, weight of the wheelchair, weight of the user, and other items such as those detailed in FIG. 5. The DMV database/server may also store a list of the subscriber's family and friends to be notified in case of an emergency. In implementations the data contained on the DMV database/server is accessed by elements of the system 100 (such as the iCu software application or other elements) using MYSQL functions.

Referring back to FIG. 2, components used in conjunction with the accident algorithm are shown, including a rotary microelectromechanical system (MEMS) sensor 202 and a stationary MEMS sensor 204. In implementations these communicate with a widget of the iCu software running on the mobile device, such as through BLUETOOTH or other short range communications, to facilitate the accident algorithm determining whether an accident has occurred. The rotary sensor 202 is seen coupled with a wheel of the wheelchair, while the stationary sensor 204 is seen coupled with a non-rotating portion of the wheelchair.

Figure 18:
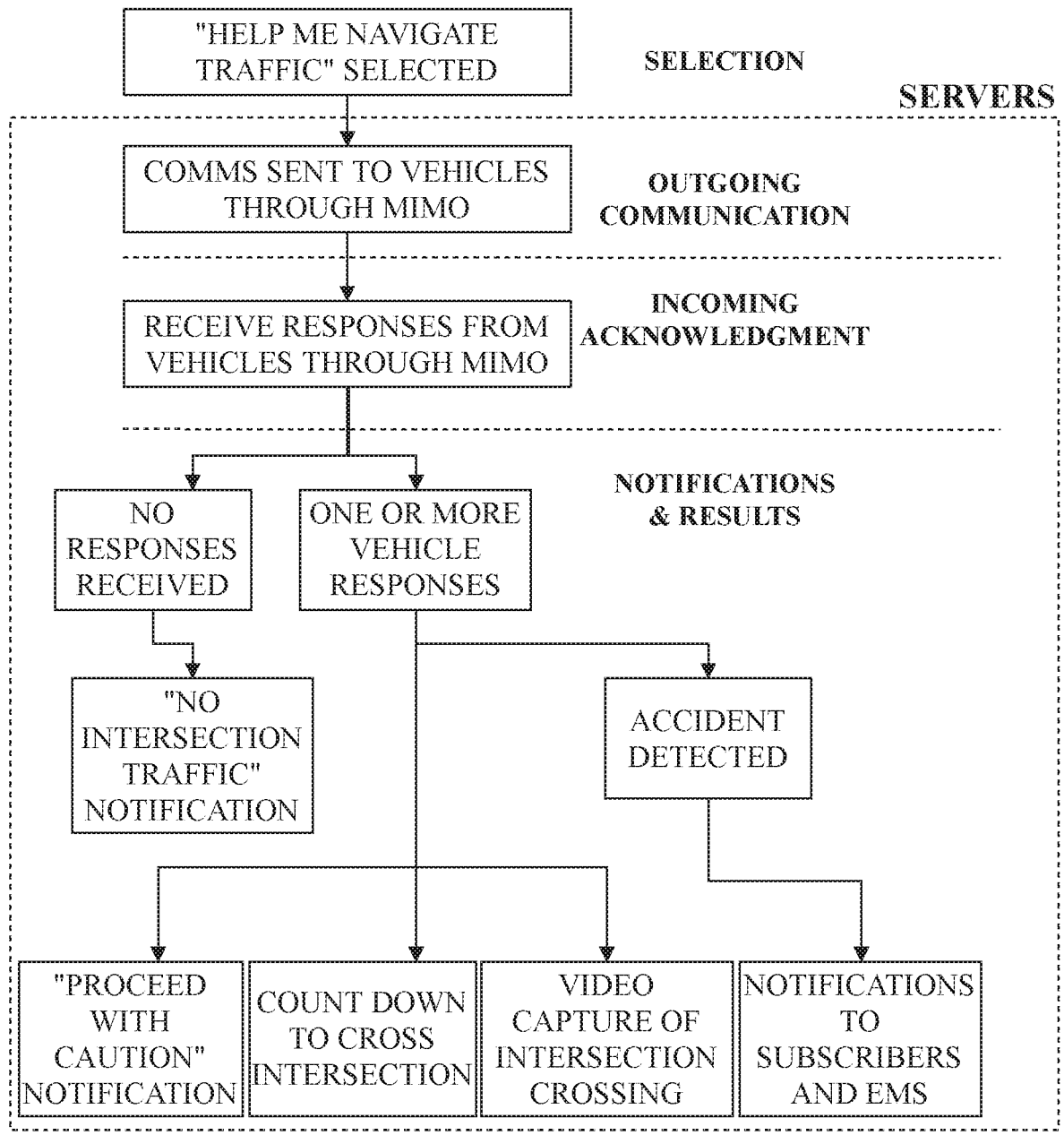
FIG. 18 is a diagram representatively illustrating a map of user interfaces implemented using the system of FIG. 1.

Referring now to FIG. 18, a block diagram representatively illustrates elements of the iCu software application structure/functions/operations. It may be seen that there is a "selection" function which simply indicates, in this example, the user selecting the "HELP ME NAVIGATE TRAFFIC" selector. The remaining functions are handled by servers, as indicated, and include an outgoing communication (communications sent to vehicles through the MIMO tower), and incoming acknowledgement (responses received from vehicles through the MIMO tower), and a number of notifications and results. For example, if no responses are received, a "NO INTERSECTION TRAFFIC" notification may be received by the phone and displayed/audibly read to the user. This may include a user interface that displays the phrase. If there are one or more vehicle responses a "PROCEED WITH CAUTION" notification may be given to the user as a visual and/or audio notification. The count down to cross the intersection may also be given as one or more visual/audio notifications. The video capture of the intersection crossing may also be handled by the system, as indicated previously. If an accident is detected, notifications may be sent to subscribers (e.g., the notification persons identified by the user) and to emergency medical services.

Figure 19:
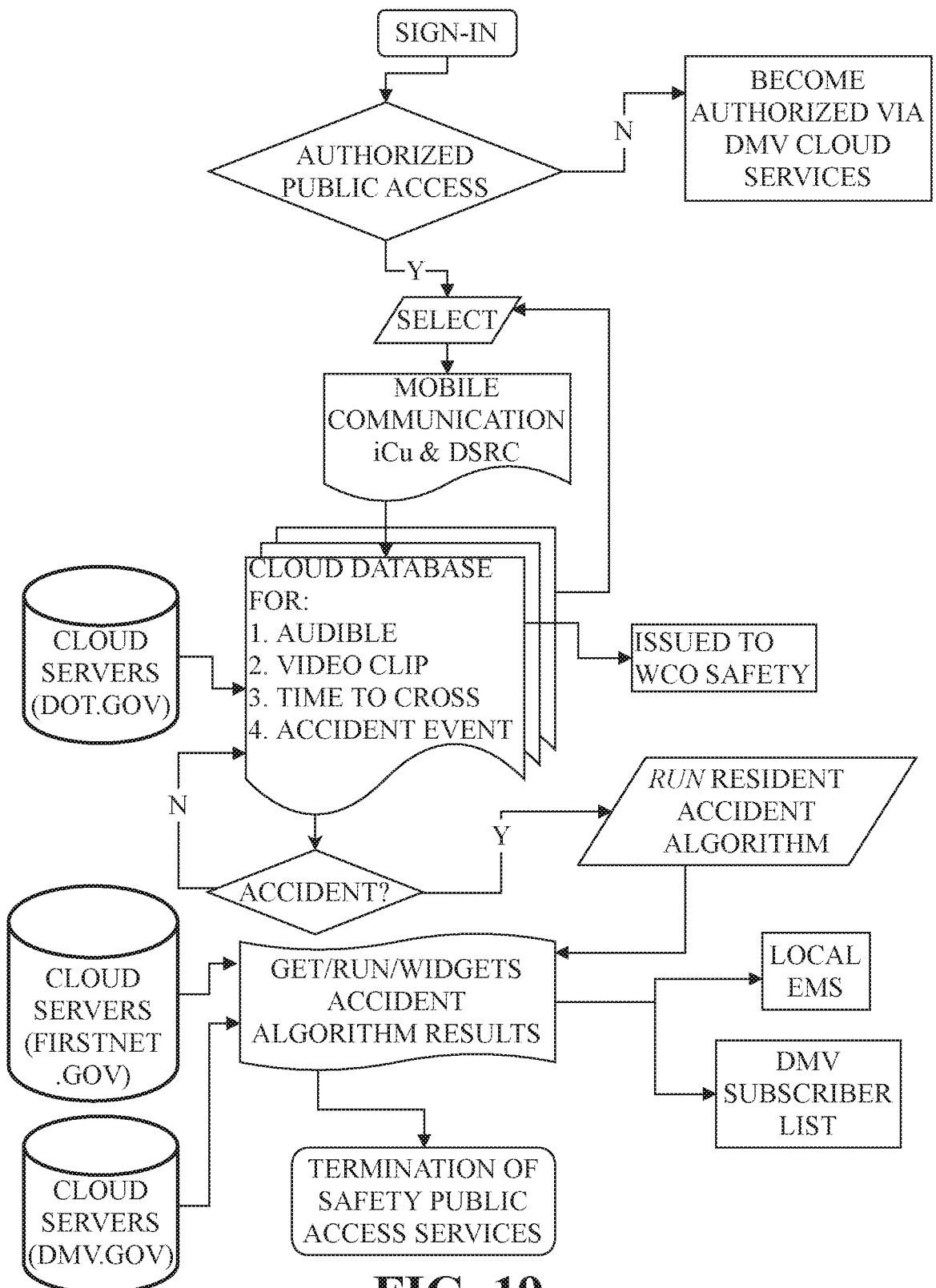
FIG. 19 is a flowchart representatively illustrating elements and methods implemented using the system of FIG. 1.

Referring now to FIG. 19, a diagram representatively illustrates a layout of source code elements used to implement the iCu software application. The diagram illustrates the functional flow of data and the safety features derived therefrom. In implementations this 2D mobile hybrid software application is built on the FLUTTER IDE Framework using the DASH software code, in a four-tiered or layered environment for scaling. In addition, the iCu software application includes a resident accident algorithm (described in FIG. 20). In implementations the software application could alternatively be written in JAVA.

Figure 20:
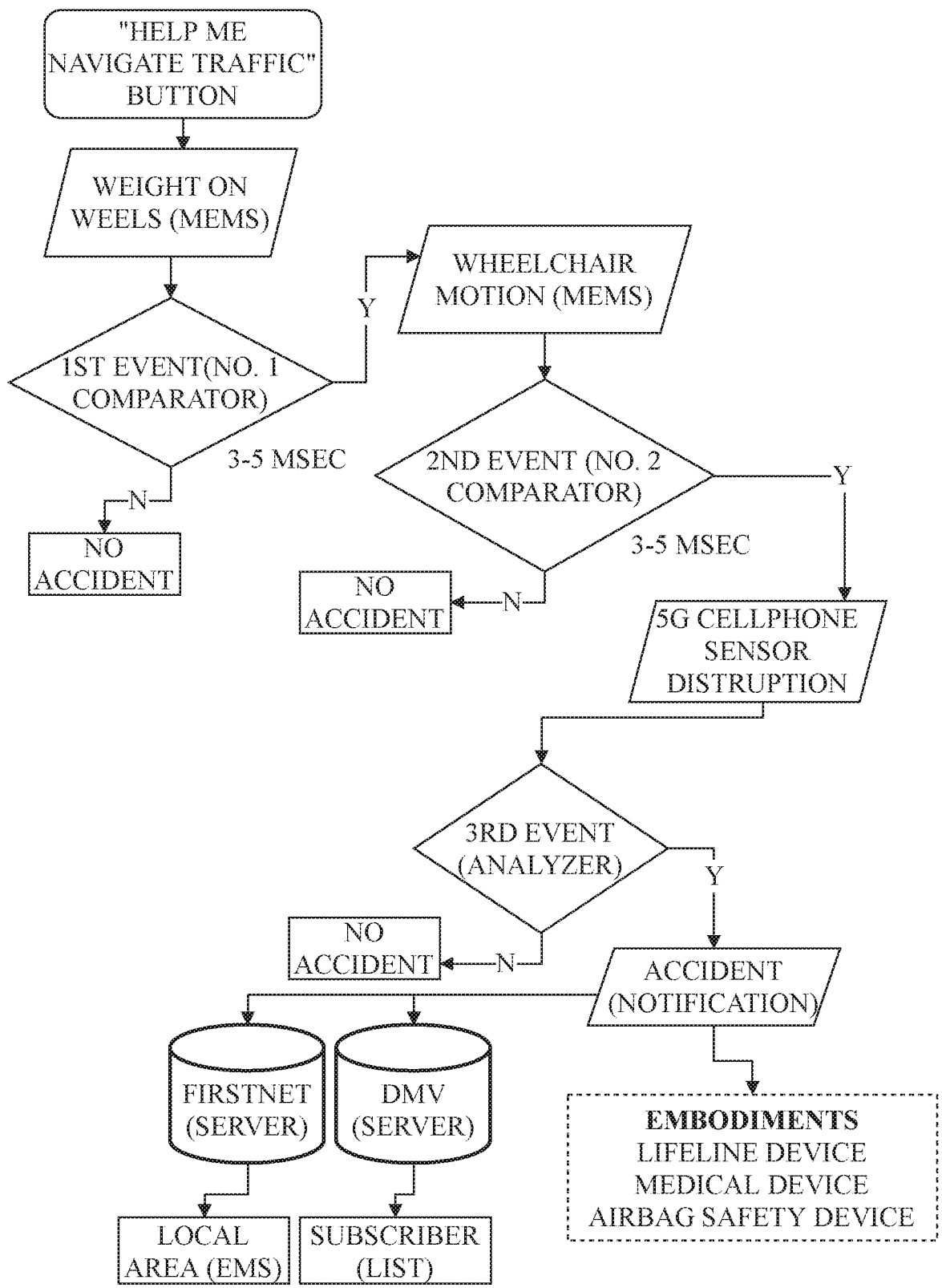
FIG. 20 is a flowchart representatively illustrating elements and methods implemented using the system of FIG. 1.

Referring now to FIG. 20, a flow diagram of the accident algorithm software layout is representatively illustrated. This diagram representatively illustrates the 3-condition events that determine the profile of a wheelchair operator's accident and, as a result, the subsequent issuing of notifications to local EMS services and the subscriber's listed family/friends on record (as stored in one or more data stores of the system 100 and/or DMV server/database). In this representative example the algorithm is a 3-event condition algorithm widget used to determine an accident profile, meaning that all three fault-events must be true before emergency notifications are issued.

Figure 21:
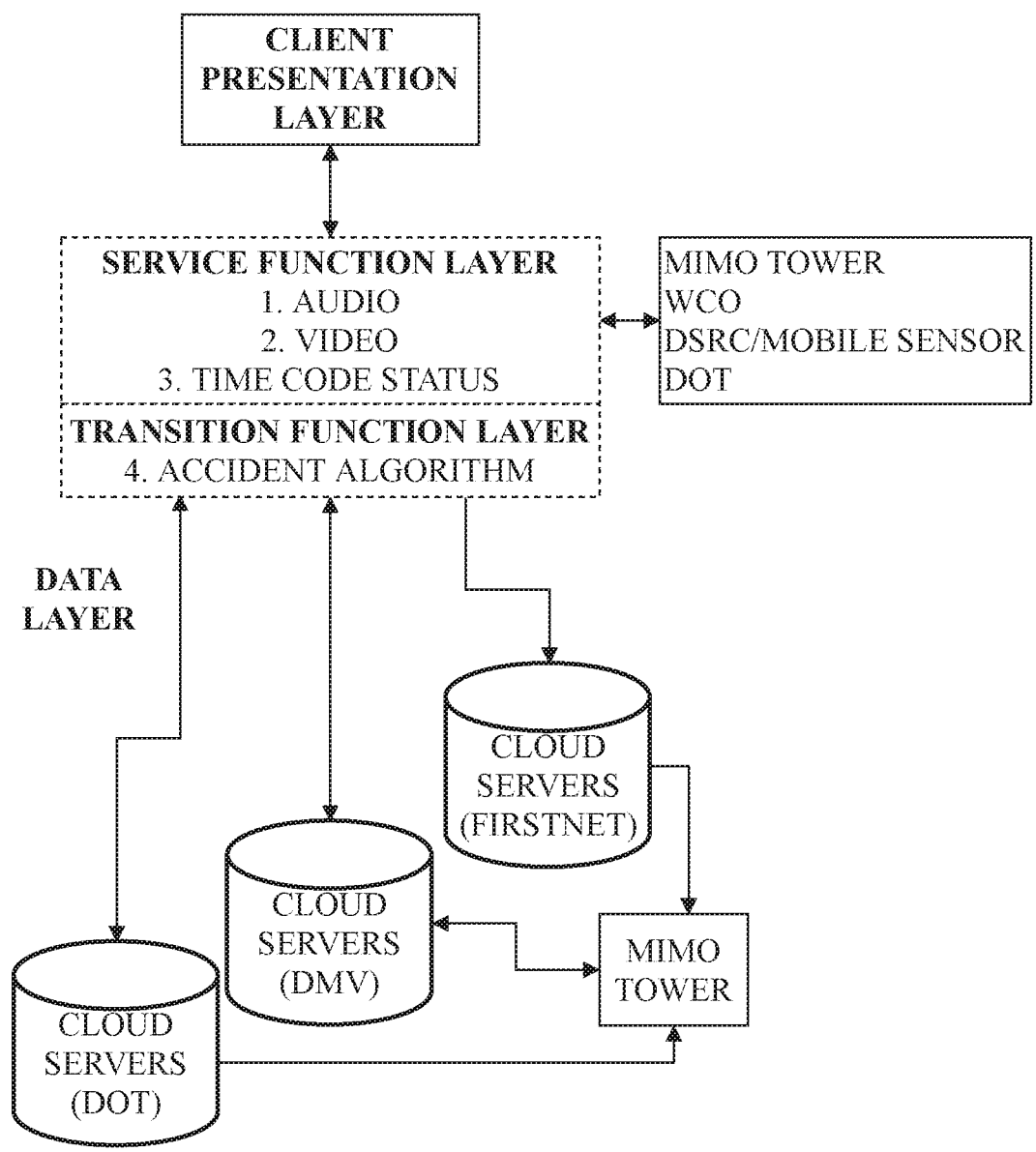
FIG. 21 is a diagram representatively illustrating elements and methods implemented using the system of FIG. 1.

Referring now to FIG. 21, a four-tier structure of the iCu software application architecture is representatively illustrated. This diagram illustrates four layers of the iCu software application along with each layer's interconnect features. The Presentation (or Client Presentation) Layer displays safety-response screens to wheelchair operators, such as the user interfaces shown in the drawings. In implementations the user interfaces may be implemented using Scalable Vector Graphics (SVG) and may include any number of interfaces/screens. The user interfaces may be The Service Function Layer (Application Layer) includes the functional widgets used to implement the four safety features of the iCu software application as described above. The Transition Function Layer (Transition Layer) is a form or portion of the Application Layer and includes the functionality of Accident Algorithm. The Data Layer includes edge server data that is commonly presented to public facility nodes. The accident algorithm utilizes the resident mobile device sensors as well as input from the MEMS sensors to determine changing wheelchair attitude and/or other items, as will be discussed hereafter, to determine an accident. The wheelchair's attitude is, in implementations, a function of its speed, acceleration, and/or position.

An example of an accident algorithm may be/include a subroutine run by elements of system 100. The subroutine may use signal outputs from two external MEMS sensors. The stationary MEMS 204 provides analog/digital pressure data to determine weight-on-wheels output. The rotary MEMS 202 provides analog/digital radian moment data to determine motion (momentum) output. The subroutine uses three sensors of the phone as a trigger to define or label the simultaneous occurrence of three collective faults. These are: (1) the global positioning system (GPS) sensor, which determines attitude and orientation of the wheelchair operator; (2) the accelerometer; and (3) the gyroscope which determine speed and direction of the wheelchair operator. When the stationary MEMS, rotary MEMS, and mobile device sensors all detect certain things, for example by non-limiting example for a simultaneous period of at least 3, or at least 5, or at least 3-5 milliseconds, an accident is determined and emergency notifications are initiated.

Referring now to TABLE 1 below, a number of states are described.

TABLE 1

| Code | Event | Use Case | Operational Mode |
|------|-------|----------|------------------|
| 000 | 1 | WCO not seated in wheelchair | Normal Operation (START) |
| | 2 | Wheelchair motionless | |
| | 3 | iCu software application not enabled | |
| NA | 1 | WCO not seated in wheelchair | Abnormal operation |
| | 2 | Wheelchair in motion | |
| | 3 | iCu software application not enabled | |
| NA | 1 | WCO not seated in wheelchair | Abnormal operation |
| | 2 | Wheelchair in motion | |
| | 3 | iCu software application enabled | |
| 011 | 1 | WCO seated in registered wheelchair | Normal operation |
| | 2 | Wheelchair motionless | |
| | 3 | iCu software application enabled | |
| 110 | 1 | WCO seated in registered wheelchair | Normal operation |
| | 2 | Wheelchair in motion @ >0 fpm to max fpm | |
| | 3 | iCu software application enabled | |
| NA | 1 | WCO in wheelchair but +/−15 lbs. noncompliant | Abnormal weight nulls accident algorithm |
| | 2 | Wheelchair in motion @ >0 fpm to max fpm | |
| | 3 | iCu software application enabled | |
| NA | 1 | WCO in wheelchair but +/−15 lbs. noncompliant | Abnormal weight & disabled app nulls accident algorithm |
| | 2 | Wheelchair in motion @ >0 fpm to max fpm | |
| | 3 | iCu software application not enabled | |
| 101 | 1 | WCO not in wheelchair | Noncompliant weight nulls accident algorithm |
| | 2 | Wheelchair in motion | |
| | 3 | iCu software application enabled | |
| 111 | 1 | Weight decreases <50% registered weight for at least 3-5 msecs at the same time as events 2 & 3 | An accident has occurred as identified by the simultaneous 3 events. Emergency notifications sent in 30 seconds. |
| | 2 | Wheelchair motion stops for at least 3-5 msecs at the same time as events 1 & 3 | |
| | 3 | iCu enabled. Mobile device sensors disrupted for at least 3-5 msecs the same time as events 1 & 2 | |

Non-active state (000) indicates the wheelchair at rest or is powered off (or that the sensors are powered off, for instance), or that the user has not yet selected the "HELP ME NAVIGATE TRAFFIC" selector. The accident state is (111). When the (111) state is reached, an emergency notification is issued.

TABLE 1 lists use case class codes (000, 011, 110, 101, and 111) to indicate normal states and the accident state. The code NA indicates "not assigned" for an abnormal state. While there may be innumerable use cases associated with wheelchair operations, the representative use cases shown in TABLE 1 are examples to distinguish between some normal states, abnormal states, and the accident state, using the logic of the accident algorithm. Not all normal and abnormal states are specifically detailed, but only a few examples are given. For example, in some settings forward motion could be considered normal and backwards motion could indicate an abnormal condition.

It is seen that code 000 (normal operation) refers to the wheelchair operator (WCO) being seated in the wheelchair, the wheelchair being motionless, and the iCu application not being enabled (i.e., the user has not selected the "HELP ME NAVIGATE TRAFFIC" selector. An abnormal state exists if the WCO is not seated in the wheelchair while it is in motion and the iCu app is not enabled ("HELP ME NAVIGATE TRAFFIC" not selected). An abnormal state exists if the WCO is not seated in the wheelchair while it is in motion and the iCu app is enabled ("HELP ME NAVIGATE TRAFFIC" has been selected). Code 011 (normal operation) refers to the WCO being in a registered wheelchair, the wheelchair being motionless, and the iCu app being enabled (the user has selected the "HELP ME NAVIGATE TRAFFIC" selector). Code 110 (normal operation) indicates the WCO is seated in a registered wheelchair, the wheelchair is in motion between a range of greater than 0 feet per minute (fpm) but less than some maximum rate (which could be, for example, 20 fpm, 30 fpm, 40 fpm, 50 fpm, 60 fpm, 70 fpm, 80 fpm, 90 fpm, 100 fpm, and so forth) and the iCu application is enabled. The accident algorithm is nulled (code NA) if the weight in the wheelchair is 15 pounds over or under the registered weight, the wheelchair is in motion between a range of greater than 0 feet per minute (fpm) but less than some maximum rate, and the iCu app is enabled. The accident algorithm is nulled (code NA) if the weight in the wheelchair is 15 pounds over or under the registered weight, the wheelchair is in motion between a range of greater than 0 feet per minute (fpm) but less than some maximum rate, and the iCu app is not enabled. Code 101 indicates a nulled accident algorithm when WCO is not in the wheelchair, the wheelchair is in motion, and the iCu application is enabled. Code 111 indicates an accident, and is triggered when three events occur simultaneously such as, by non-limiting example, for at least 3 milliseconds, or at least 5 milliseconds, or at least 3-5 milliseconds: (1) the weight decreases to (or less than) 50% of the registered weight; (2) the wheelchair motion stops as detected by the rotary MEMS sensor; (3) the iCu app is enabled (the user has selected "HELP ME NAVIGATE TRAFFIC" selector) and the GPS/accelerometer/gyro sensors of the phone indicate a disruption.

The disruption of the mobile device sensors may be a change in the data beyond a certain threshold and/or a simultaneous change in data at similar/identical rates. For example, the GPS data/values, accelerometer data/values, and gyroscope data/values of a mobile device are constantly changing as a user is moving. A "disruption" in these values (all happening simultaneously) may refer to, by non-limiting example, the three sensors simultaneously having a shift that is a threshold percentage greater or less than a certain percentage of the previous value and so is unexpected, indicating a sudden increase or decrease in value. This could distinguish between normal changes in the values/data of these sensors and data/values that would tend to indicate an accident. By non-limiting example, a disruption could be a sudden shift of 15% or more in each sensor (each sensor within a 3-5 msec window having a value 15% greater or less than the previous value). Other methods for determining a "disruption" are possible, and this is only one example. Another example, of the sensor values all shifting up or down at the same rate, is described further below. This sudden shift for each sensor is an example of a change in sensed values beyond a predetermined threshold which indicates a disruption.

Accordingly, in this example the conditions that would identify an accident are (1) the weight on wheels falling to or below a certain value, (2) motion stopping as detected by the rotary MEMS sensor, and (3) simultaneous disruption of the three mobile device sensors after the "HELP ME NAVIGATE TRAFFIC" selector has been selected. These simultaneous events, labeled as Code "111," would evidence the accident state. In implementations, after the three events have been simultaneously determined (as an example for at least 3-5 msec), then 30 seconds thereafter the emergency notifications are issued. The accident state is temporary in implementations, and after the emergency notification is sent the iCu application is reset, with the user needing to select the "HELP ME NAVIGATE TRAFFIC" button again to activate it.

The accident in this example is defined as three independent events occurring simultaneously within an at least 3 millisecond (or at least 5 millisecond, or at least 3-5 millisecond) event-window. In some implementations one or more of the events would also need to persist for 30 seconds (for example the weight on wheels stays at or below the threshold for 30 seconds, the wheels stay motionless for 30 seconds, etc.) In other implementations the events do not need to persist beyond the 3-5 msec. These determinations are used as data inputs in a controlling object-oriented program (accident algorithm). If an accident state has been determined by the simultaneous occurrence of the three events, then emergency notifications are issued, which in implementations may be issued a predetermined amount of time after the three events simultaneously occur, as indicated above with the example of 30 seconds. As stated above, it is not possible to list every scenario, and those given in TABLE 1 are only representative examples.

As indicated previously, in implementations the system operates in conjunction with government agencies requiring user registration. At the time of registration the wheelchair operator provides the make and model of the wheelchair (for weight determination) and the body weight of the operator. In some implementations changing either of these weight parameters (or changing them beyond a certain percentage or certain amount of pounds) may nullify the functions of the accident algorithm or trigger a notification to the user to update the information.

In implementations the accident algorithm is turned on with the selection of the "HELP ME NAVIGATE TRAFFIC" button. The accident algorithm, in implementations, only runs within the communicative range of the MIMO tower (for example, within a 120 yard radius or diameter of a MIMO tower). In implementations, once the wheelchair operator is removed from the MIMO tower range, the accident algorithm becomes dormant, later to be reactivated by another selection of the "HELP ME NAVIGATE TRAFFIC" selector. When the wheelchair operator exits the communicative range of a MIMO tower, a notification may be displayed or communicated through the iCu app, for example a visual notification "Wheelchair Operator out of MIMO Area" along with a sound notification, or the like.

In FIG. 2 the sensor is shown in the seat of the wheelchair itself. In other implementations the sensor could be for example proximate an axle of the wheelchair and could take into account the weight of the wheelchair upon the axle so that the system assumes a combined weight of the wheelchair and the wheelchair operator. In other implementations the sensor could be in or on a wheel (or both wheels) and/or there could be multiple of these sensors in/on the wheels to regularly detect the combined weight of the wheelchair and wheelchair operator. The system may be configured to accept a weight within a given range (by non-limiting example, +/−15 lbs.) as indicating that the user is in the wheelchair. This range may be adjusted in implementations by the user—for example if the user is carrying a package or pet or the like the system may notify the user that the weight seems off and the user may be able to indicate that the weight is accurate due to an item being carried. Or for example of the user has gained or lost weight recently they similarly may indicate this so that the weight is updated.

The rotary MEMS in implementations may have an operational range, for example between 0 and 20 revolutions per minute (rpm), though in other implementations it could be higher such as up to 30, 50, 50, 60, 79, 80, 90, 100, and so forth, rpm.

In the examples described in the drawings the MIMO tower communicates with the DMV, DOT and FIRSTNET cloud servers. In other implementations other servers of system 100 could be situated communicatively between the MIMO tower and other third party cloud servers, or any data from third party servers/databases that are needed to implement the system/methods could be downloaded onto other system servers to be used to implement the system.

The hybrid mobile iCu software application is dedicated to support the safety of wheelchair operators to reduce the risk of traffic accidents with manually driven and autonomous vehicles by communicating the presence of the wheelchair operators within a 5G cellular infrastructure, while in traffic, through four safety functions derived from and processed through cloud servers. The iCu software application captures edge cloud server data and communicates stored and local real time data capture to wheelchair operators, reducing the risk of accidents with manually driven and autonomous vehicles.

In implementations the following four safety features are derived from and driven by the iCu software application: (1) a directive to "PROCEED WITH CAUTION" is communicated to the wheelchair operator after communicating his/her presence to nearby vehicles; (2) a local area time-to-cross status is downloaded from cloud data services to the mobile device of the wheelchair operator identifying the time remaining to cross the intersection; (3) a real-time video clip of the intersection crossing of the wheelchair operator is downloaded to the wheelchair operator's mobile device; and (4) in the event of an accident, as determined by a resident 3-condition accident algorithm, notifications are transmitted to local EMS personnel and to family/friends of the wheelchair operator as listed in a DMV database/server and/or other system database(s)/server(s). These four safety functions are triggered and deployed automatically, without the involvement of the wheelchair operator. In implementations once the wheelchair operator has exited the local area of the MIMO tower these safety functions are automatically terminated.

In some implementations machine learning (ML) could be used to determine what events actually indicate an accident, such as by training an ML model on one or more datasets that include accidents and non-accidents, so that the ML model is trained to determine, based on an actual scenario, whether the events indicate a likely accident, to then trigger the emergency notifications.

A software such as the aforementioned accident algorithm may involve state sampling, such as stationary MEMS sampling to determine weight on wheels (issuing a 1 code if the weight is outside a given range or 0 if it is within it), rotary MEMS sampling to determine attitude and velocity/positioning of the wheelchair (issuing a 1 code if the velocity/attitude indicates no motion and a 0 code if it indicates motion), and a comparator of the mobile device may determine whether a disruption of the sensor data has occurred (issuing a 1 code if it has and a 0 if it hasn't). In such an example the (111) code indicates all of these events occurring, and if they occur simultaneously for 3-5 msec then an accident event has occurred. The sampling process may include conversion of analog input data to digital data.

Digital data may be used to output a binary value (0 or 1) based on a function or comparator or the like. When all three events indicate a TRUE state the accident is defined and the emergency notifications are initiated by the MIMO tower sending signals to the relevant servers for emergency notifications to EMS and to family/friend subscribers. However, in other implementations the three-number codes (011, 110, 101, etc.) are arbitrarily assigned to certain event scenarios and are not necessarily directly related to binary TRUE/FALSE outcomes for certain conditions. In TABLE 1 the codes are arbitrarily assigned so that, for example, the system/methods determine whether the three events in each case are present and, if so, the corresponding code is issued, which may be accomplished by defining the codes and triggering events in the software/system as desired in a number of ways.

Figure 23:
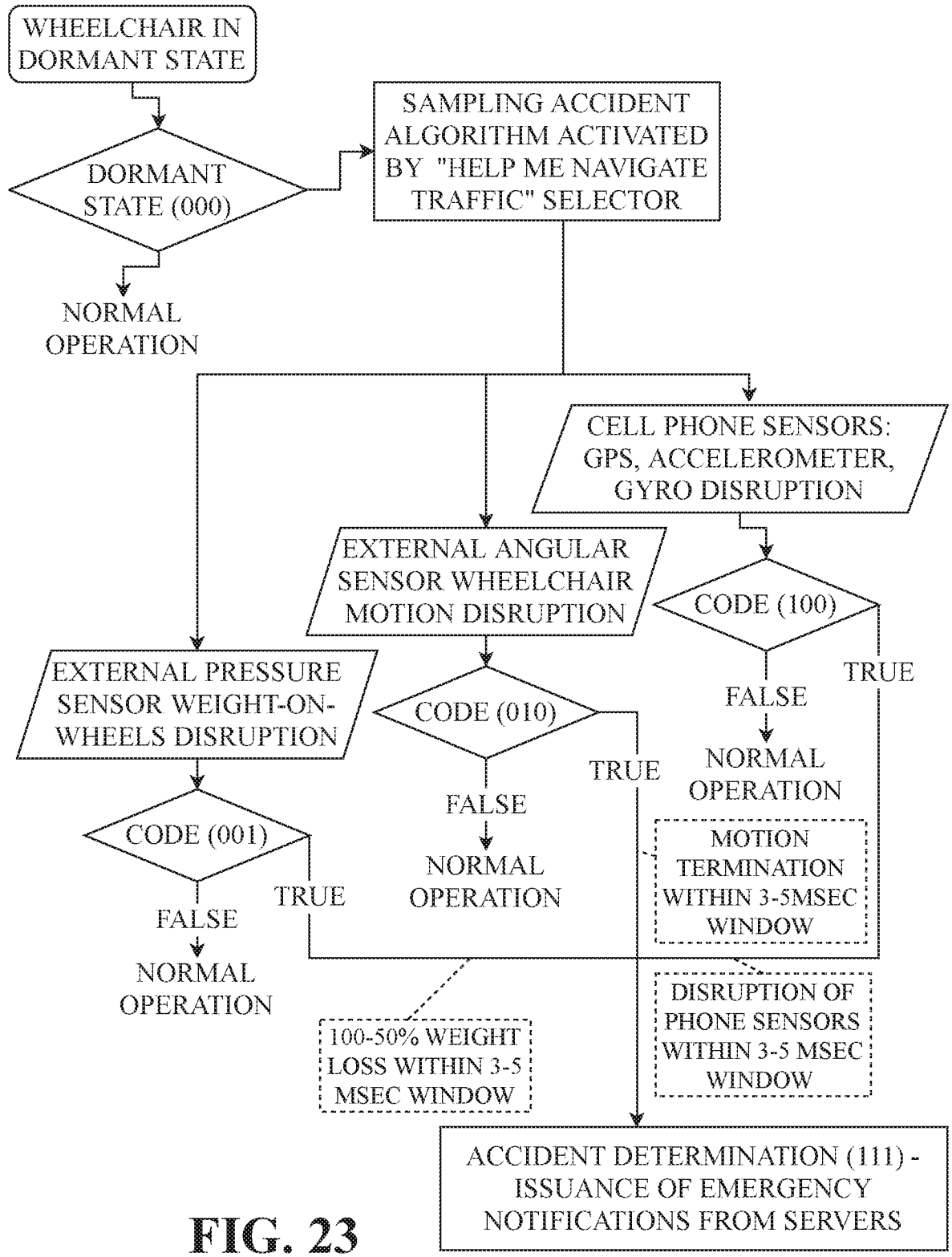
FIG. 23 is a diagram representatively illustrating elements and methods implemented using the system of FIG. 1.

FIG. 23 representatively illustrates, using a block diagram, several elements of an accident algorithm similar to that discussed above. In the example of FIG. 23 the (001) represents a disruption in weight-on-wheels within a certain range based on input from the stationary MEMS, the (010) code represents disruption of sensed wheelchair motion using the rotary MEMS, and the (100) code represents disruption of the cell phone sensors (GPS, accelerometer, and gyroscope) as has been discussed above, for example within a 3-5 msec window. In this example the (001), (010) and (100) codes sum to form the (111) code when the accident condition is present.

Figure 24:
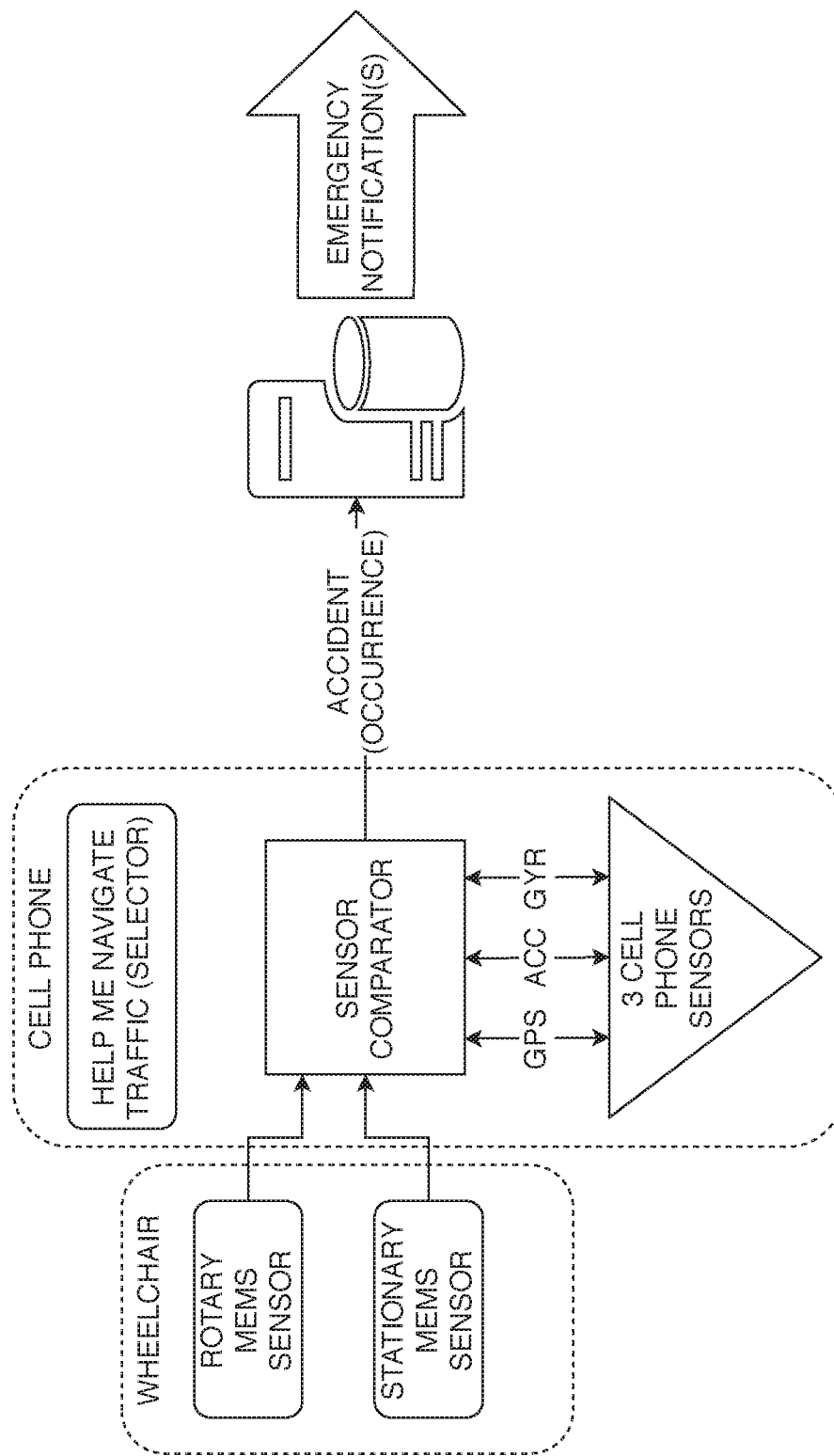
FIG. 24 is a diagram representatively illustrating elements and methods implemented using the system of FIG. 1.

Referring now to FIG. 24, an additional diagram is given for describing aspects of implementations of wheelchair safety systems. The wheelchair of the wheelchair operator is representatively diagrammed and includes the rotary MEMS sensor and the stationary MEMS sensor. The cell phone, which in implementations may be a 5G cell phone, is representatively illustrated and includes the "HELP ME NAVIGATE TRAFFIC" selector. The cell phone sensors are representatively illustrated along with GPS, accelerometer (ACC), and gyroscope (GYR) data. A sensor comparator is representatively illustrated. When an accident is detected, communications between the cell phone and the aforementioned servers/databases results in the emergency notification(s) being sent out.

Accordingly, in implementations the iCu software application is activated by pressing the "HELP ME NAVIGATE TRAFFIC" selector. Through this sole action the accident algorithm is activated to begin value readings of the external MEMS sensors and the internal cell phone sensors. The safety functions of the iCu application in implementations are active and only within a 120 yard radius of a MIMO tower communicatively coupled with remote supporting cloud servers.

In implementations the two external MEMS sensors (rotary & stationary) provide motion values and weight-on-wheels values to the software comparator function of the accident algorithm, a subroutine of the iCu application. These external MEMS values are continuously monitored by the comparator function to identify the occurrence of an accident. Since the values of the stationary MEMS and rotary MEMS are continuously monitored by the comparator function, when the value of the rotary MEMS goes to 0 feet per minute (fpm) and the stationary MEMS registered weight-on-wheels is reduced by more than 50% within a 3-5 msec window, then a possible accident may have occurred.

In implementations the three internal cell phone sensors (GPS, accelerometer and gyroscope) continuously send parity values to the comparative function of the accident algorithm to determine the occurrence of an accident. Since the values submitted to registers associated with the cell phone sensors are always changing (both up and down independently), in implementations the accident algorithm determines that when the values of these sensors fall or rise simultaneously at the same rate of change (a disruption) with respect to each cell phone sensor, within the shared 3-5 msec window, a possible accident may have occurred.

In implementations the accident algorithm is defined as including a three-event accident state. When the comparator function has sampled input values from the external MEMS sensors (rotary MEMES value is 0 fpm and stationary MEMS value is greater than 50% weight reduction) and the three cell phone sensors output values changing simultaneously at the same rate (up or down), an accident has occurred. This simultaneous change at the same rate (up or down) is an example of a change in sensed values beyond a predetermined threshold (the predetermined threshold here being that all values change in the same direction and/or at the same rate, or about the same rate meaning within 15% of one another's rates—for example only two values changing in the same direction or at about the same rate would be below the predetermined threshold to indicate a disruption in cell phone sensor values, in this implementation). Accordingly, external MEMS values are compared with the internal cell phone sensor parity readings to determine an accident condition. Once an accident has been determined, in implementations 30 seconds thereafter emergency notifications are initiated using the servers to communicate with local emergency caregivers and to inform registered family members and/or friends/others that an accident has occurred.

In implementations the accident algorithm is a subroutine and controlled by the software application as described in pseudo code terms. In such implementations the software subroutine uses signal outputs from the stationary and rotary MEMS sensors. The stationary MEMS provides analog/digital pressure data to determine weight on wheels output. The rotary MEMS sensor provides analog/digital radian moment data to determine motion (momentum) output. Additionally, this software subroutine also uses three of the twelve sensors of a 5G cell phone as a trigger to define or label the simultaneous occurrences of three collective faults. These are the GPS sensor (determining attitude and orientation of the wheelchair operator), the accelerometer and the gyroscope (determining speed and direction of the wheelchair operator). When these three cell phone sensors are simultaneously momentarily disrupted an accident event has occurred, which is followed by emergency notifications. The three events are used to determine an accident and are a logic trigger configured to invoke the issuance of emergency notifications from/using the respective servers.

In implementations the accident algorithm is a major subroutine of the iCu software application. In implementations the function of the accident algorithm is to determine by its collective methods if the registered wheelchair operator has been in a traffic accident as defined by a comparison of the use case class codes (of TABLE 1) of the external MEMS sensors (stationary and rotary) with the internal cell phone sensors (accelerometer, GPS, and gyro).

In implementations the iCu application and/or other system elements will access dynamic data on the FIRSTNET, DMV and/or DOT servers by searching using MYSQL of the "edge" in order to download safety data (for example in a 5G low latency manner) for the wheelchair operator, such as using cloud server software development kits (SDKs). This safety data is available to the wheelchair operator while in the 120 yard perimeter of the MIMO tower, as has been described above.

As described above, the iCu software application in implementations is activated by granting government agencies offering the public services to registered wheelchair operators. At the time of registration wheelchair operators may provide the make and model of the wheelchair used along with the body weight of the wheelchair operator. Changing either of these parameters may nullify the function of the accident algorithm and/or may trigger the request for updated information or for confirmation of changed information/data.

In a non-active state the wheelchair is vacant of an operator and motionless. The cell phone in this situation is not connected to the external MEMS sensors (rotational and stationary) using the BLUETOOTH or other communication mechanisms. The iCu software application and its accident algorithm subroutine are dormant.

Once the wheelchair operator is stationed in the wheelchair, with the cell phone turned on, and the iCu software application is opened and the user has selected the "HELP ME NAVIGATE TRAFFIC" selector, the external MEMS pressure sensor may registers a use case class code of (001) as it calculates the sum of weights of the registered wheelchair (equipment) with the weight of the operator's body as use case class code (001) for weight on wheels. As described above, in other implementations the code (001) may indicate a disruption of weight on wheels. In this implementation, however, after the wheelchair has been manned by the operator, with the phone turned on and the iCu software application engaged, when the wheelchair operator places the wheelchair in motion (either manually or by automatic power), with a forward/backward momentum, the MEMS motion sensor captures analog data and converts and calculates angular motion into linear digital data, thus establishing the motion of the wheelchair operator as use case class code (010). As described above, in other implementations the code (010) could indicate a disruption in motion. In this implementation, however, while in service of the iCu software application, the use case class codes can change into the following use case configurations denoting normal operation: (110), (011), (101). This is dependent on the mission attitude of the wheelchair operator.

In some implementations the use case codes are not "summed" to get the accident state (111). For example, in implementations in which the (001) code indicates weight on wheels within an appropriate range of values, and in which the (010) code indicates motion of the wheelchair, the accident code (111) may simply be an assigned code (arbitrarily assigned) and not a "sum" of three other codes. However, as also described above, the (001), (010) and (100) codes could, in implementations, all represent disruptions related to motion, weight on wheels, and cell phone sensors, in which case the software application and/or accident algorithm may sum the individual codes to reach the (111) accident code.

The accident algorithm may use the MEMS sensor data and/or use case class codes shown in TABLE 1 and data from the cell phone sensors to determine an accident event.

In places where the phrase "one of A and B" is used herein, including in the claims, wherein A and B are elements, the phrase shall have the meaning "A or B." This shall be extrapolated to as many elements as are recited in this manner, for example the phrase "one of A, B, and C" shall mean "A, B, or C," and so forth.

In places where the description above refers to specific implementations of wheelchair safety systems and related methods, one or more or many modifications may be made without departing from the spirit and scope thereof. Details of any specific implementation/embodiment described herein may, wherever possible, be applied to any other specific implementation/embodiment described herein.

What is claimed is:

1. A wheelchair system, comprising:
   one or more servers;
   a software application provided by the one or more servers to be installed on a computing device communicatively coupled with the one or more servers through a telecommunications network; and
   one or more user interfaces displayed on the computing device using the software application, the one or more user interfaces displaying a traffic navigation selector configured to receive a selection indicating that a wheelchair operator is preparing to cross a street;
   wherein the software application is configured to:
      receive an input from one or more sensors of the computing device (hereinafter "computing device sensors");
      determine, at least partly in response to receiving the input from the one or more computing device sensors, whether the wheelchair operator has been involved in an accident; and
      in response to determining that the wheelchair operator has been involved in the accident, automatically initiate sending of an accident notification to emergency personnel.

2. The system of claim 1, wherein the one or more computing device sensors comprise a global positioning system (GPS) sensor, an accelerometer, and a gyroscope.

3. The system of claim 1, wherein the software application is configured to determine, at least partly in response to receiving an input from one or more sensors coupled with a wheelchair (hereinafter "wheelchair sensors"), whether the wheelchair operator has been involved in the accident.

4. The system of claim 3, wherein one of the one or more wheelchair sensors is configured to sense a weight.

5. The system of claim 3, wherein one of the one or more wheelchair sensors is configured to sense motion of the wheelchair.

6. The system of claim 3, wherein the software application is configured to determine that the accident has occurred by determining that: the one or more wheelchair sensors have indicated that the wheelchair is not in motion; the one or more wheelchair sensors have indicated that a weight has dropped below a predetermined threshold, and; the one or more computing device sensors have indicated a change in sensed values beyond a predetermined threshold.

7. The system of claim 1, wherein the software application is configured to, in response to the selection of the traffic navigation selector, provide a notification of an amount of time left to cross the street.

8. The system of claim 1, wherein the software application is configured to, in response to the selection of the traffic navigation selector, initiate visual recording of the wheelchair operator crossing the street using a camera communicatively coupled with the computing device through the telecommunications network.

9. The system of claim 1, further comprising one or more data stores communicatively coupled with the one or more servers, wherein the one or more user interfaces comprise an interface for initiating storing, in the one or more data stores, contact information of a contact person, and wherein the software application is configured to, in response to determining that the wheelchair operator has been involved in the accident, automatically send an accident notification to the contact person.

10. The system of claim 1, wherein the software application is configured to, in response to the selection of the traffic navigation selector, automatically initiate sending of one or more first signals, wherein the software application is configured to determine that one or more vehicles are within a predetermined area by receiving one or more return signals responsive to the one or more first signals, wherein the software application is configured to determine no vehicles are within the predetermined area by receiving no signals responsive to the one or more first signals within a predetermined amount of time, and wherein the software application is configured to notify the wheelchair operator, only after the software application has determined whether one or more vehicles are within the predetermined area, to proceed crossing the street.

11. The system of claim 1, wherein the software application is configured to initiate, in response to the selection of the of the traffic navigation selector, receiving the input from the one or more computing device sensors.

12. The system of claim 1, wherein the software application is configured to stop receiving the input from the one or more computing device sensors when the wheelchair operator reaches a predetermined distance from a communication node.

13. A wheelchair system, comprising:
one or more servers;
a software application provided by the one or more servers to be installed on a computing device communicatively coupled with the one or more servers through a telecommunications network; and
one or more user interfaces displayed on the computing device using the software application, the one or more user interfaces displaying a traffic navigation selector configured to receive a selection indicating that a wheelchair operator is preparing to cross a street;
wherein the software application is configured to, in response to the selection of the traffic navigation selector, automatically initiate sending of one or more first signals;
wherein the software application is configured to determine that one or more vehicles are within a predetermined area by receiving one or more return signals responsive to the one or more first signals;
wherein the software application is configured to determine that no vehicles are within the predetermined area by receiving no signals responsive to the one or more first signals within a predetermined amount of time; and
wherein the software application is configured to notify the wheelchair operator, only after the software application has determined whether one or more vehicles are within the predetermined area, to proceed crossing the street.

14. A method of use of a wheelchair system, comprising:
providing one or more servers;
providing a software application, using the one or more servers, to be installed on a computing device communicatively coupled with the one or more servers through a telecommunications network;
displaying one or more user interfaces on the computing device using the software application, wherein one of the one or more user interfaces comprises a traffic navigation selector;
receiving a selection of the traffic navigation selector using the one or more user interfaces, the selection of the traffic navigation selector indicating that a wheelchair operator is preparing to cross a street;
receiving an input, using the software application, from one or more sensors of the computing device (hereinafter "computing device sensors");
receiving an input, using the software application, from one or more sensors coupled with a wheelchair (hereinafter "wheelchair sensors");
determining, using the software application, at least partly in response to receiving the input from the one or more computing device sensors and the input from the one or more wheelchair sensors, whether the wheelchair operator has been involved in an accident; and
in response to determining that the wheelchair operator has been involved in the accident, automatically initiating sending of an accident notification to emergency personnel.

15. The method of claim 14, wherein the input from the one or more computing device sensors and the one or more wheelchair sensors comprises one or more of: global positioning system (GPS) sensor data; accelerometer sensor data; gyroscope sensor data; weight data; and wheelchair motion data.

16. The method of claim 14, further comprising determining, using the software application, that the accident has occurred by determining that: the one or more wheelchair sensors have indicated that the wheelchair is not in motion; the one or more wheelchair sensors have indicated that a weight has dropped below a predetermined threshold, and; the one or more computing device sensors have indicated a change in sensed values beyond a predetermined threshold.

17. The method of claim 14, further comprising providing, using the software application, in response to the selection of the traffic navigation selector, a notification of an amount of time left to cross the street.

18. The method of claim 14, further comprising, using the software application, in response to the selection of the traffic navigation selector, initiating visual recording of the wheelchair operator crossing the street using a camera communicatively coupled with the computing device through the telecommunications network.

19. The method of claim 14, further comprising communicatively coupling one or more data stores with the one or more servers, wherein the one or more user interfaces comprise an interface for initiating storing in the one or more data stores contact information of a contact person, and wherein the method includes automatically sending an accident notification to the contact person, using the software application, in response to determining that the wheelchair operator has been involved in the accident.

20. The method of claim 14, further comprising determining, using the software application, whether one or more vehicles are within a predetermined area based on whether one or more return signals have been received in response to one or more first signals, wherein the method further comprises notifying the wheelchair operator, using the software application, only after determining whether one or more vehicles are within the predetermined area, to proceed crossing the street.

* * * * *

UNITED STATES PATENT AND TRADEMARK OFFICE
CERTIFICATE OF CORRECTION

Page 1 of 2

PATENT NO. : 10,660,806 B1
APPLICATION NO. : 16/743506
DATED : May 26, 2020
INVENTOR(S) : Blanche Michelle Nelson-Herron and Gary B. Justice It is certified that error appears in the above-identified patent and that said Letters Patent is hereby corrected as shown below:

In the Specification

Column 1, Line 22 change "wheelchair-pedestrian" to -wheelchair pedestrians-.
Column 2, Line 35 change "of the of the" to -of the-.
Column 5, Line 11 change "and are" to -and wheelchairs are-.
Column 5, Line 13 change "to be move" to -to move-.
Column 6, Line 21 change "of FIG. 1" to -of FIG. 1)-.
Column 6, Line 22 change "system" to -systems-.
Column 6, Line 53 change "are" to -is-.
Column 6, Line 56 change "Th" to -The-.
Column 6, Line 64 change "accidents of" to -of accidents of-.
Column 7, Line 35 change "through a sole" to -a sole-.
Column 10, Line 62 change "server and a signal sent" to -server, and a signal is sent-.
Column 11, Line 29 change "determined" to -determine-.
Column 14, Line 39 delete "The user interfaces may be".
Column 14, Line 45 change "of Accident Algorithm" to -of the Accident Algorithm-.
Column 14, Line 65 change "determine" to -determines-.
Column 14, Line 67 delete "for example".
Column 15, Line 44 change "at rest" to -is at rest-.
Column 15, Line 66 change "selector" to -selector)-.
Column 16, Line 2 change "not selected" to -is not selected-.
Column 17, Line 67 change "for example of" to -for example if-.
Column 18, Line 6 change "30, 50, 50, 60, 79, 80, 90, 100" to -30, 40, 50, 60, 70, 80, 90, 100-.
Column 18, Line 14 change "system/methods" to -systems/methods-.
Column 19, Line 12 change "system/methods" to -systems/methods-.
Column 19, Line 19 change "(001)" to -(001) code-.
Column 19, Line 49 change "and only" to -only-.
Column 20, Line 11 change "MEMES" to -MEMS-.
Column 20, Line 32 change "and controlled" to -and is controlled-.
Column 21, Line 21 change "registers" to -register-.

Signed and Sealed this
Thirtieth Day of June, 2020

Andrei Iancu
*Director of the United States Patent and Trademark Office*

CERTIFICATE OF CORRECTION (continued)
U.S. Pat. No. 10,660,806 B1

In the Claims

Column 23, Lines 17-18 change "of the of the" to -of the-.